(12) United States Patent
Wang

(10) Patent No.: US 7,556,806 B2
(45) Date of Patent: Jul. 7, 2009

US007556806B2

(54) CARBOHYDRATE-BASED SYNTHETIC VACCINES FOR HIV

(75) Inventor: Lai-Xi Wang, Ellicott City, MD (US)

(73) Assignee: University of Maryland Biotechnology Institute, Baltimore, MD (US)

( * ) Notice: Subject to any disclaimer, the term of this patent is extended or adjusted under 35 U.S.C. 154(b) by 410 days.

(21) Appl. No.: 10/531,124

(22) PCT Filed: Oct. 14, 2003

(86) PCT No.: PCT/US03/32496

§ 371 (c)(1),
(2), (4) Date: Jun. 30, 2005

(87) PCT Pub. No.: WO2004/033663

PCT Pub. Date: Apr. 22, 2004

(65) Prior Publication Data

US 2005/0244424 A1    Nov. 3, 2005

Related U.S. Application Data

(60) Provisional application No. 60/417,764, filed on Oct. 11, 2002.

(51) Int. Cl.
*A61K 39/00* (2006.01)
(52) U.S. Cl. .................................................. 424/184.1
(58) Field of Classification Search ....................... None
See application file for complete search history.

(56) References Cited

FOREIGN PATENT DOCUMENTS

WO    WO 98/04272    *    2/1998
WO    WO 00/18432    *    4/2000

OTHER PUBLICATIONS

Wittmann et al., Spatial Screening of Lectin Lignads. Cyclic Peptides as Scaffolds for Multivalent Presentation of Carbohydrates, Peptides: The Wave of the Future, American Peptide Society, 2001, pp. 174-176.*
Mascola, J. R.; Snyder, S. W.; Weislow, O. S.; Belay, S. M.; Belshe, R. B.; Schwartz, D. H.; Clements, M. L.; Dolin, R.; Graham, B. S.; Gorse, G. J.; Keefer, M. C.; McElrath, M. J.; Walker, M. C.; Wagner, K. F.; McNeil, J. G.; MeCutchan, F. E.; Burke, D. S. Immunization with envelope subunit vaccine products elicits neutralizing antibodies against laboratory-adapted but not primary isolates of human immunodeficiency virus type 1. *J Infect Dies* 1996, 173, 340-348.
Alcott, T. C.; Betake, F. R.; Burke, D. S.; Redfield, R. R.; Bird, D. L. Lack of induction of antibodies specific for conserved, discontinuous epitopes of HIV-1 envelope glycoprotein by candidate AIDS vaccines. *J Immunol* 1995, 155, 4100-4110.
Schwartz, D. H.; Gorse, G.; Clements, M. L.; Belshe, R.; Izu, A.; Duliege, A. M.; Berman, P.; Twaddell, T.; Stablein, D.; Sposto, R.; et al. Induction of HIV-1-neutralizing and syncytium-inhibiting antibodies in uninfected recipients of HIV-IIIIB rgp120 subunit vaccine. *Lancet* 1993, 342, 69-73.

Burton, D. R. A vaccine for HIV type 1: the antibody perspective. *Proc Natl Acad Sci USA* 1997, 94, 10018-10023.
Wyatt, R.; Sodroski, J. The HIV-1 envelope glycoproteins: fusogens, antigens, and immunogens. *Science* 1998,280, 1884-1888.
Sattentan, Q. J.; Moulard, M.; Brivet, B.; Botto, F.; Guillemot, J. C.; Mondor, I.; Poignard, P.; Ugolini, S. Antibody neutralization of HIV-1 and the potential for vaccine design. *Immunol Lett.* 1999, 66, 143-149.
Nabel, G. J.; Challenges and opportunities for development of an AIDS vaccine. *Nature* 2001, 410, 1002-1007.
Burton, D. R.; Pyati, J.; Koduri, R.; Sharp, S. J.; Thornton, O.B.; Parren, P. W.; Sawyer, L. S.; Hendry, R. M.; Dunlop, N.; Nara, P. L.; et al. Efficient neutralization of primary isolates of HIV-1 by a recombinant human monoclonal antibody. *Science* 1994, 266, 1024-1027.
Trkola, A.; Purtscher, M.; Muster, T.; Ballaun, C.; Buchacher, A.; Sullivan, N.; Srinivasan, K.; Sodroski, J.; Moore, J. P.; Katinger, H.; Human monoclonal antibody 2G12 defines a distinctive neutralization epitope on the gp120 glycoprotein of human immunodeficiency virus type 1. *J Virol* 1996, 70, 1100-1108.
Conley, A. J.; Kessler, 3. A., 2nd; Boots, L. J.; Tung, J. S.; Arnold, B. A.; Keller, P. M.; Shaw, A. R.; Emini, E. A. Neutralization of divergent human immunodeficiency virus type 1 variants and primary isolates by IAM-41-2F5, an anti-gp41 human monoclonal antibody. *Proc. Natl. Acad Sci. U & A.* 1994, 91, 3348-3352.
Zwick, M. B.; Labrijn, A. F.; Wang, M.; Speniehauer, C.; Saphire, E. O.; Binley, J. M.; Moore, J. P.; Stiegler, G.; Katinger, H.; Burton, D. R.; Parren, P. W. Broadly neutralizing antibodies targeted to the membrane-proximal external region of human immunodeficiency virus type 1 glycoprotein gp41. *J Virol* 2001, 75, 10892-10905.
Mascola, J. R.; Stiegler, G.; VanCott, T. C.; Katinger, H.; Carpenter, C. B.; Hanson, C. E.; Beary, H.; Hayes, D.; Frankel, S. S.; Birx, D. L.; Lewis, M. G.; Protection of macaques against vaginal transmission of a pathogenic HIV- 1/SIV chimeric virus by passive infusion of neutralizing antibodies. *Nat Med* 2000, 6,207-210.
Baba, T. W.; Liska, V.; Hofmann-Lehmann, R.; Vlasak, J.; Xu, W.; Ayehunie, S.; Cavacini, L. A.; Posner, M. R.; Katinger, H.; Stiegler, G.; Bernacky, B. J.; Rizvi, T.A.; Schmidt, R.; Hill, L. R.; Keeling, M. E.; Lu, Y.; Wright, J. E.; Chou, T. C.; Ruprecht, R. M. Human neutralizing monoclonal antibodies of the IgG1 subtype protect against mucosal simian-human immunodeficiency virus infection. *Nat Med* 2000, 6, 200-206.
DeVico, A.; Silver, A.; Thronton, A. M.; Sarngadhran, M. G.; Pal, R. Covalently crosslinked complexes of human immunodeficiency virus type 1 (HIV-1) gp120 and CD4 receptor elicit a neutralizing immune response that includes antibodies selective for primary virus isolates. *Virology* 1996, 218,258-263.

(Continued)

*Primary Examiner*—Bruce Campell
*Assistant Examiner*—Nicole Kinsey White
(74) *Attorney, Agent, or Firm*—Marianne Fuierer; Moore & Van Allen PLLC

(57) ABSTRACT

The present invention relates to a constructed oligosaccharide cluster, optionally bonded to an immunogenic protein, that can be administered to a subject to induce an immune response for increasing production of 2G12 and/or used in assays as reactive sites for determining compounds that inactivate and/or bind the high-mannose oligosaccharide cluster. Compositions comprising these clusters, methods of using these clusters and compositions are disclosed.

10 Claims, 16 Drawing Sheets

OTHER PUBLICATIONS

LaCasse, R. A.; Follis, K. E.; Trahey, M.; Scarborough, J. D.; Litttman, D. R.; Nunberg, J. H. Fusion-competent vaccines: broad neutralization of primary isolates of HIV. *Science* 1999, 283, 357-362.

Leonard, C. K.; Spellman, M. W.; Riddle, L.; Harris, R. J.; Thomas, J. N.; Gregory, T. J. Assignment of intrachain disulfide bonds and characterization of potential glycosylation sites of the type 1 recombinant human immunodeficiency virus envelope glycoprotein (gp120) expressed in Chinese hamster ovary cells. *J Biol Chem* 1990, 265, 10373-10382.

Mizuochi, T.; Matthews, T. J.; Kato, M.; Hamako, J.; Titani, K.; Solomon, J.; Feizi, T. Diversity of oligosaccharide structures on the envelope glycoprotein gp120 of human immunodeficiency virus 1 from the lymphoblastoid cell line H9. Presence of complex-type oligosaccharides with bisecting N- acetylglucosamine residues. *J Biol Chem* 1990, 265, 8519-8524.

Geyer, H.; Holschbach, C.; Hunsmann, G.; Schneider, J. Carbohydrates of human immunodeficiency virus. Structures of oligosaccharides linked to the envelope glycoprotein 120. *J Biol Chem* 1988, 263, 11760-11767.

Zhu, X.; Borchers, C.; Bienstock, R. J.; Tomer, K. B. Mass spectrometric characterization of the glycosylation pattern of HIV- gp120 expressed in CHO cells. *Biochemistry* 2000, 39, 11194-11204.

Kwong, P. D.; Wyatt, R.; Robinson, J.; Sweet, R. W.; Sodroski, J.; Hendrickson, W. A. Structure of an HIV gp120 envelope glycoprotein in complex with the CD4 receptor and a neutralizing human antibody. *Nature* 1998, 393, 648-659.

Wyatt, R.; Kwong, P. D.; Desjardins, E.; Sweet, R. W.; Robinson, J.; Hendrickson, W. A.; Sodroski, J. G. The antigenic structure of the HIV gp120 envelope glycoprotein. *Nature* 1998, 393, 705-711.

Gerencer, M.; Barrett, P. N.; Kistner, O.; Mitterer, A.; Dorner, F. Natural IgM antibodies in baby rabbit serum bind high-mannose glycans on HIV type 1 glycoprotein 120/160 and activate classic complement pathway. *AIDS Res Hum Retroviruses* 1998, 14, 599-605.

Arendrup, M.; Sonnerborg, A.; Svennerholm, B.; Akerblom, L.; Nielsen, C.; Clausen, H.; Olofsson, S.; Nielsen, J. O.; Hansen, J. E. Neutralizing antibody response during human immunodeficiency virus type 1 infection: type and group specificity and viral escape. *J Gen Virol* 1993, 74, 855-863.

Hansen, J. E.; Nielsen, C.; Clausen, H.; Mathiesen, L. R.; Nielsen, J. O. Effect of anti-carbohydrate antibodies on HIV infection in a monocytic cell line (*U937*). *Antiviral Res* 1991, 16, 233-242.

Tomiyama, T.; Lake, D.; Masuho, Y.; Hersh, E. M. Recognition of human immunodeficiency virus glycoproteins by natural anti-carbohydrate antibodies in human serum; *Biochem Biophys Res Commun* 1991, 177, 279-285.

Cunto-Amesty, G.; Dam, T. K.; Luo, P.; Monzavi-Karbassi, B.; Brewer, C. F.; Van Cott, T. C.; Kieber-Emmons, T. Directing The immune response to carbohydrate antigens. *J Biol Chem* 2001, 276, 30490-30498.

Ezekowitz, R. A.; Kuhlman, M.; Groopman, J. E.; Bym, R. A. A human serum mannose-binding protein inhibits in vitro infection by tile human immunodeficiency virus. *J Exp Med* 1989, 169, 185-196.

Hansen, J. E.; Nielsen, C. M.; Nielsen, C.; Heegaard, P.; Mathiesen, L. R.; Nielsen, J. O. Correlation between carbohydrate structures on the envelope glycoprotein gp120 of HIV-1 and HIV-2 and syncytium inhibition with lectins. *Aids* 1989, 3, 635-641.

Balzarini, J.; Schols, D.; Neyts, J.; Van Damme, E.; Peumans, W.; De Clercq, E. Alpha-(1-3)- and alpha-(1 -6)-D-mannose-specific plant lectins are markedly inhibitory to human immunodeficiency virus and cytomegalovirus infections in vitro. *Antimicrob Agents Chemother* 1991, 35, 410416.

Gattegno, L.; Ramdani, A.; Jouault, T.; Saffar, L.; Gluckman, J. C. Lectin-carbohydrate interactions and infectivity of human immunodeficiency virus type 1 (HIV-1) *AIDS Res Hum Retroviruses* 1992, 8, 27-37.

Hammar, L.; Hirsch, I.; Machado, A. A.; De Mareuil J.; Baillon, J. G.; Bolmont, C.; Chermann, J. C. Lectin-mediated effects on IIIV type 1 infection in vitro. *AIDS Res Hum Retroviruses* 1995, 11, 87-95.

Saifuddin, M.; Hart, M. L.; Gewurz, H.; Zhang, Y.; Spear, G. T. Interaction of mannose-binding lectin with primary isolates of human immunodeficiency virus type 1. *J Gen Virol* 2000, 81, 949-955.

Boyd, M. R.; Gustafson, K. R.; MeMahon, J. B.; Shoemaker, W H.; OKeefe, B. R.; Mori, T.; Gulakowski, R. J.; Wu, L.; Rivera, M. I.; Laurencot, C. M.; Currens, M. J.; Cardellina, J. H., 2nd; Buckheit, R. W., Jr.; Nara, P. L.; Pannell, L. K.; Sowder, R. C., 2nd; Henderson, L. E. Discovery of cyanovirin-N, a novel human immunodeficiency virus- inactivating protein that binds viral surface envelope glycoprotein gp120: potential applications to microbicide development. *Antimicrob Agents Chemother* 1997, 41, 1521-1530.

Dey, B.; Lemer, D. L.; Lusso, P.; Boyd, M. R.; Elder, J. H.; Berger, E. A. Multiple antiviral activities of cyanovirin-N: blocking of human immunodeficiency virus type 1 gp120 interaction with CD4 and coreceptor and inhibition of diverse enveloped viruses. *J Virol* 2000, 74, 4562-4569.

Bewley, C. A. Solution structure of a cyanovirin-N:Man alpha 1-2Man alpha complex:structural basis for high-affinity carbohydrate-mediated binding to gp120. *Structure (Camb)* 2001, 9, 931-940.

Bewley, C. A.; Otero-Quintero, S. The potent anti-HIV protein cyanovirin-N contains two novel carbohydrate binding sites that selectively bind to Man(8) D1D3 and Man(9) with nanomolar affinity implications for binding to the HIV envelope protein gp120. *J Am Chem Soc* 2001, 123, 3892-3902.

Bolmstedt, A. J.; O'Keefe, B. R.; Shenoy, S. R.; McMahon, J. B.; Boyd, M. R. Cyanovirin-N defines a new class of antiviral agent targeting N-linked, high-mannose glycans in an oligosaccharide-specific manner. *Mol Pharmacol* 2001, 59, 949-954.

Geijtenbeek, T. B.; Kwon, D. S.; Torensma, R.; van Vliet, S. J.; van Duijnhoven, G. C.; Middel, J.; Cornelissen, I. L.; Nottet, H. S.; KewalRamani, V. N., Littman, D. R.; Figdor, C.G.; van Kooyk, Y. DC-SIGN, a dendritic cell-specific HIV-1-binding protein that enhances trans-infection of T cells. *Cell* 2000, 100, 587-597.

Geijtenbeek, T. B.; Torensma, R.; van Vliet, S. J.; van Duijnhoven, G. C.; Adema, G. J.; van Kooyk:, Y.; Figdor, C. G. Identification of DC-SIGN, a novel dendritic cell-specific ICAM-3 receptor that supports primary immune responses. *Cell* 2000, 100, 575-585.

Pohlmann, S.; Soilleux, E. J.; Baribaud, F.; Leslie, G. J.; Morris, L. S.; Trowsdale, J.; Lee, B.; Coleman, N.; Doms, R. W. DC-SIGNR, a DC-SIGN homologue expressed in endothelial cells, binds to human and simian immunodeficiency viruses and activates infection in trans. *Proc Natl Acad Sci USA* 2001, 98, 2670-2675.

Feinberg, H.; Mitchell, D. A.; Drickamer, K.; Weis, W. I. Structural basis for selective recognition of oligosaccharides by DC- SIGN and DC-SIGNR. *Science* 2001, 294, 2163-2166.

Wang, L. X.; Ni, J.; Singh, S. Carbohydrate-centered maleimide cluster as a new type of templates for multivalent peptide assembling: Synthesis of multivalent HIV-1 gp41 peptides. *Bioorg. Med.Chem.* 2002, in press.

Kudryashov, V., Kim, H. M.; Ragupathi, G.; Danishefsky, S. J.; Livingston, P.O.; Lloyd, K. O. Immunogenicity of synthetic conjugates of Lewis(y) oligosaccharide with proteins in mice: towards the design of anticancer vaccines. *Cancer Immunol Immunother* 1998, 45, 281-286.

Slovin, S. F.; Ragupathi, G.; Adluri, S.; Ungers, G.; Terry, K.; Kim, S.; Spassova, M.; Bornmann, W. G.; Fazzari, M.; Dantis, L.; Olkiewicz, K.; Lloyd, K. O.; Livingston, P. O.; Danishefsky, S. J.; Scher, H. I. Carbohydrate vaccines in cancer: immunogenicity of a fully synthetic globo H hexasaccharide conjugate in man. *Proc Nail Acad &Sci U S A* 1999, 96, 5710-5715.

Wang, Z. O.; Williams, L. J.; Zhang, X. F.; Zatorski, A.; Kudryashov, V.; Ragupathi, G.; Spassova, M.; Borumarm, W.; Slovin, S. F.; Scher, H. I.; Livingston, P.O.; Lloyd, K. O.; Danishefsky, S. J. Polyclonal antibodies from patients immunized with a globo H-keyhole limpet hemocyanin vaccine: isolation, quantification, and characterization of immune responses by using totally synthetic immobilized tumor antigens. *Proc Nail Acad Sci USA* 2000, 97, 2719-2724.

Sabbatini, P. J.; Kudryashov, V.; Ragupathi, G.; Danishefsky, S. J.; Livingston, P.O.; Bornmann, W.; Spassova, M.; Zatorski, A.; Spriggs, D.; Aghajanian, C.; Soignet, S.; Peyton, M.; O'Flaherty, C.; Curtin, J.; Lloyd, K. O. Immunization of ovarian cancer patients with a synthetic Lewis (y)- protein conjugate vaccine: a phase 1 trial. *Int J Cancer* 2000, 87, 79-85.

Danishefsky, S. J.; Allen, J. W From the laboratory to the clinic: A retrospective on fully synthetic carbohydrate-based anticancer vaccines *Angew. Chem. Int. Ed Engi.* 2000, 39, 836-863.

Kudryashov, V.; Glunz, P. W.; Williams, L. J.; Hintermann, S.; Danishefsky, S. J.; Lloyd, K. O. Toward optimized carbohydrate-based anticancer vaccines: epitope clustering, carrier structure, and adjuvant all influence antibody responses Lewis (y) conjugates in mice. *Proc Natl Acad & Sci USA* 2001, 98, 3264-3269.

Gilewski, T.; Ragupathi, G.; Bhuta, S.; Williams, L. J.; Musselli, C.; Zhang, X. F.; Bencsath, K. P.; Panageas, K. S.; Chin, J.; Hudis, C. A.; Norton, L.; Houghton, A. N.; Livingston, P.O.; Danishefsky, S. J. Immunization of metastatic breast cancer patients with a fully synthetic globo H conjugate: a phase 1 trial. *Proc Natl Acad & Sci USA* 2001, 98, 3270-3275.

Allen, J. R.; Harris, C. R.; Danishefsky, S. J. Pursuit of optimal carbohydrate-based anticancer vaccines: preparation of a multiantigenic unimolecular glycopeptide containing the Tn, MBrI, and Lewis (y) antigens. *J Am Chem Soc.* 2001, 123, 1890-1897.

Ragupathi, G.; Cappello, S.; Yi, S. S.; Canter, D.; Spassova, M.; Bornmann, W. G.; Danishefsky, S. J.; Livingston, P.O. Comparison of antibody titers after immunization with monovalent or tetravalent KLH conjugate vaccines. *Vaccine* 2002, 20, 1030-1038.

Morley, S. L.; Pollard, A. J. Vaccine prevention of meningococcal disease, coining soon? *Vaccine* 2001, 20, 666-687.

Lis, H.; Sharon, N. Soybean agglutinin—a plant glycoprotein. Structure of the carbohydrate unit. *J Biol Chem* 1978, 253, 3468-3476.

Dorland, L.; van Halbeek, H.; Vleigenthart, J. F.; Lis, H.; Sharon, N. Primary structure of the carbohydrate chain of soybean agglutinin. A reinvestigation by high resolution $^1$H NMR spectroscopy. *J Biol Chem* 1981, 256, 7708-7711.

Wang, L. X.; Fang, J. Q.; Lee, Y. C. Chemoenzymatic synthesis of a high-mannose-type N-glycopeptide analog with C-glycosidic linkage. *Tetrahedron Lett.* 1996, 37, 1975-1978.

Wang, L. X.; Tang, M.; Suzuki, T.; Kitajima, K.; Inoue, Y.; Inoue, S.; Fang, J. Q.; Lee, Y. C. Combined chemical and enzymatic synthesis of a C-glycopeptide and its inhibitory activity toward glycoamidases. *J Am. Chem. Soc.* 1997, 119, 11137-11146.

Ni, J.; Singh, S.; Wang, L. X. Improved preparation of perallylated cyclodextrins: facile synthesis of cyclodextrin-based polycationic and polyanionic compounds. *Carbohydr Res* 2002, 337, 217-220.

Sprengard, Ux.; Kretzschmar, G.; Bartnik, E.; Huls, C.; Kunz, H. Synthesis of an RGD-sialyl-Lewis glycoconjugates: A new highly active ligand for P-selectin. *Angew Chem.Intt. Ed Engl* 1995, 34 ,990-993.

Cohen-Anisfeid, S. T.; Lansbury Jr., P. T. A practical, convergent method for glycopeptide synthesis. *J Am. Chem. Soc.* 1993, 115, 10531-10537.

Helling, F.; Shang, A.; Calves, M.; Zhang, S.; Ren, S.; Yu, R. K.; Oettgen, H. F.; Livingston, P.O. GD3 vaccines for melanoma: superior immunogenicity of keyhole limpet hemocyanin conjugate vaccines. *Cancer Res* 1994, 54, 197-203.

Helling, F.; Zhang, S.; Shang, A.; Adluri, S.; Calves, M.; Koganty, R.; Longenecker, B. M.; Yao, T. J.; Oettgen, H. F.; Livingston, P.O. GM2-KLH conjugate vaccine: increased immunogenicity in melanoma patients after administration with immunological adjuvant QS-21. *Cancer Res* 1995, 55, 2783-2788.

Kensil, C. R.; Patel, U.; Lennick, M.; Marciani, D. Separation and characterization of saponins with adjuvant activity from Quillaja saponaria Molina cortex. *J Immunol* 1991, 146, 431-437.

Pal, R.; DeVico, A.; Rittenhouse, S.; Sarngadharan, M. G. Conformational perturbation of the envelope glycoprotein gp120 of human immunodeficiency virus type 1 by soluble CD4 and the lectin succinyl Con A. *Virology* 1993, 194, 833-837.

DeVico, A. L.; Rahman, R.; Welch, J.; Crowley, R.; Lusso, P.; Sarngadharan, M. G.; Pal, R. Monoclonal antibodies raised against covalently crosslinked complexes of human immunodeficiency virus type 1 gp120 and CD4 receptor identify a novel complex-dependent epitope on gp 120. *Virology 1995*, 211, 583-588.

Fouts, T. R.; Tuskan, R. G.; Chada, S.; Hone, D. M.; Lewis, G. K. Construction and immunogenicity of Salmonella typhimurium vaccine vectors that express HIV-1 gp120. *Vaccine* 1995, 13, 1697-1705.

Dear, E. S.; Li, X. L.; Moodily, T.; Ho, D. D. High concentrations of recombinant soluble CD4 are required to neutralize primary human immunodeficiency virus type 1 isolates. *Proc. Natl. Acad. Sci. USA.* 1990, 87, 6574-6578.

Connor, R. I.; Sheridan, K. B.; Ceradini, D.; Choe, S.; Landau, N. R. Change in coreceptor use coreceptor use correlates with disease progression in HIV—1 infected individuals. *J. Exp. Med* 1997, 185,621-628.

Connor, R. I.; Mohri, H.; Cao, Y.; Ho, D. D. Increased viral burden and cytopathicity correlate temporally with CD4+ T-lymphocyte decline and clinical progression in human immunodeficiency virus type 1-infected individuals. *J Virol* 1993, 67, 1772-1777.

Vujcic, L. K.; Quinnan, G. V., Jr. Preparation and characterization of human HIV type 1 neutralizing reference sera. *AIDS Res. Hum. Retroviruses*, 1995, 11, 783-787.

a) Turnbull, W. B.; Stoddatt, J. F.; *J. Biotechnol.* 2002,90,231-255. b) Lindhorst, T. K., *Topics in Curr. Chem.* 2002,218, 200-235. (c) Roy, R., *Curr. Opin. Struct Biol.* 1996, 6, 692-702.

Kitov, P.I.; Sadowska, J. M.; Mulvey, G.; Armstrong, G. D.; Ling, H.; Pannu, N. S.; Read, R. J.; Bundle, D. R., *Nature* 2000, 403, 669-672.

Wang, L. x.; Ni, J.; Singh, S., *Bioorg. Med Chem.* 2002, *in press*.

Lis, H.; Sharon, N., *J Biol. Chem.* 1978, 253, 3468-3476.

Duncan, R. J.; Weston, P. D.; Wrigglesworth, R., *Anal. Biochem.* 1983, 132, 68-73.

Mizuochi, T., Matthews, T. J., Kato, M., Hamako, J., Titani, K., Solomon, J., and Feizi, T. (1990) *J Biol Chem* 265, 8519-8524.

Geyer, H., Holschbach, C., Hunsmann, G., and Schneider, J. (1988) *J Biol Chem* 263, 11760-11767.

Zhu, X., Borchers, C., Bienstock, R. J., and Tomer, K. B. (2000) *Biochemistry* 39, 11194-11204.

Fujita, K., Tanaka, N., Sano, M., Kato, I., Asada, Y., and Takegawa, K. (2000) *Biochem. Biophys. Res. Commun.* 267, 134-138.

Huang, C. C., Mayer, H. E., and Montgomery, R. (1970) *Carbohydr. Res.* 13, 127-137.

Sanders, R. W., Venturi, M., Schiffner, L., Kalyanaraman, R., Katinger, H., Lloyd, K. O., Kwong, P. D., and Moore, J. P. (2002) *J Virol* 76, 7293-7305.

Scanlan, C. N., Pantophlet, R., Wormald, M. R., Ollmann Saphire, E., Stanfield, R., Wilson, I. A., Katinger, H., Dwek, R. A., Rudd, P. M., and Burton, D. R. (2002) *J Virol* 76, 7306-7321.

Wang, L. X., Ni, J., and Singh, S. (2003) *Bioorg. Med. Chem.* 11, 129-136.

Ni, J., Singh, S., and Wang, L. X. (2003) *Bioconjug Chem* 14, 232-238.

Duncan, R. J., Weston, P. D., and Wrigglesworth, R. (1983) *Anal Biochem* 132, 68-73.

Ann Chapman et al.; Structure of the High Mannose Oligosaccharides of a Human IgM Myeloma Protein; The Journal of Biological Chemistry; Feb. 10, 1979; pp. 816-823; vol. 254, No. 3; USA.

Kimiyasu Shiraki et al.; Processing of hepatitis B virus surface antigen expressed by recombinant Oka varicella vaccine virus; Journal of General Virology; 1992; pp. 1401-1407; 73; Great Britain.

John-Erik S. Hansen et al.; Inhibition of Human Immunodeficiency Virus (HIV) Infection In Vitro by Anticarbohydrate Monoclonal Antibodies: Peripheral Glycosylation of HIV Envelope Glycoprotein gp120 May Be a Target for Virus Neutralization; Journal of Virology; Jun. 1990; pp. 2833-2840; vol. 64, No. 6; American Society of Microbiology.

Christopher N. Scanlan et al.; The Broadly Neutralizing Anti-Human Immunodeficiency Virus Type 1 Antibody 2G12 Recognizes a Cluster of a1-2 Mannose Residues on the Outer Face of gp120; Journal of Virology; Jul. 2002; pp. 7306-7321; vol. 76, No. 14; American Society for Microbiology.

Yuko Nakahara et al.; Rationally designed synthesis of high-mannose and complex type undecasaccharides; Carbohydrate Research; 1996; pp. 67-84; 280; Elsevier Science Ltd.

Calarese, et al., Antibody Domain Exchange Is an Immunological Solution to Carbohydrate Cluster Recognition. *Science*, Jun. 27, 2003, pp. 2065-2071, vol. 300.

Dudkin, et al., Toward Fully Synthetic Carbohydrate-Based HIV Antigen Design: On the Critical Rose of Bivalency. *J. Am. Chem. Soc*, (Communication), 2004, pp. 9560-9562, vol. 126.

* cited by examiner (M = mannose; GN = GlcNAc; R = spacer)

M = mannose; GN = GlcNAc; R = spacer:

CARBOHYDRATE-BASED SYNTHETIC VACCINES FOR HIV

CROSS-REFERENCE TO RELATED APPLICATIONS

This application is filed under the provisions of 35 U.S.C. §371 and claims the priority of International Patent Application No. PCT/US2003/032496 on Oct. 14, 2003, which in turn claims priority of U.S. Provisional Patent Application No. 60/417,764 filed on Oct. 11, 2002.

BACKGROUND OF THE INVENTION

1. Field of the Invention

The present invention generally relates to vaccines, and more particularly, to an HIV vaccine comprising immunogenic high-mannose type oligosaccharide clusters that mimics the HIV carbohydrate antigen having an affinity for the HIV-1 neutralizing antibody 2G12.

2. Background of the Related Art

HIV is a member of the lentivirus family of retroviruses. Retroviruses are small-enveloped viruses that contain a single-stranded RNA genome, and replicate via a DNA intermediate produced by a virally encoded reverse transcriptase, an RNA-dependent DNA polymerase.

The HIV viral particle comprises a viral core, composed in part of capsid proteins, together with the viral RNA genome and those enzymes required for early replicative events. A myristylated gag protein forms an outer shell around the viral core, which is, in turn, surrounded by a lipid membrane envelope derived from the infected cell membrane. The HIV envelope surface glycoproteins are synthesized as a single 160-kilodalton precursor protein, which is cleaved by a cellular protease during viral budding into two glycoproteins, gp41 and gp120. gp41 is a transmembrane glycoprotein and gp120 is an extracellular glycoprotein, which remains non-covalently associated with gp41, possibly in a trimeric or multimeric form.

Based on structural analysis, HIV-1 gp120 contains multiple high-mannose type N-glycans. These discontinuous oligosaccharide chains are grouped together to form a unique oligosaccharide microdomain. This high-mannose oligosaccharide grouping to form an epitope site has not been found in any human glycoproteins and is unique to HIV-1.

The worldwide epidemic of the human immuno-deficiency virus type 1 (HIV-1) urges the development of an effective HIV vaccine. Yet, it has been difficult to design effective immunogens that are able to elicit broadly neutralizing antibodies against HIV-1 primary isolates. In addition to sequence variability of neutralizing epitopes, HIV-1 has also evolved other mechanisms to evade immune attack, including change of conformations, shielding of conserved epitopes through heavy glycosylations, and formation of compact glycoprotein complexes (envelope spikes) that hinder the accessibility of epitopes to immune responses. It becomes clear that a successful strategy in developing an effective HIV-1 vaccine relies on the identification of conserved epitopes on HIV-1 that are accessible to neutralization and on the design of epitope-based immunogens that stimulate high immune responses.

So far, only a few human monoclonal antibodies (MAbs) have been identified that are able to neutralize a broad range of HIV-1 primary isolates. These include MAbs b12 and 2G12 that target the outer envelope glycoprotein gp120, and MAbs 2F5 and 4E10 that target the inner envelope glycoprotein gp41. The broadly neutralizing abilities of these MAbs implicate the existence of conserved and accessible antigenic determinants, i.e., epitopes, on the surface of most HIV-1 primary isolates. Passive immunization using these MAbs either alone or in combination has shown that these MAbs protect against HIV-1 challenge in animal models when present at sufficient concentrations prior to or shortly after exposure(12). However, results have been limited and determinative by concentration and ongoing re-immunization.

Among the broadly HIV-1 neutralizing antibodies so far identified, the human monoclonal antibody 2G12 is the only one that directly targets the surface carbohydrate antigen of HIV-1. Several pieces of evidence suggest that the epitope of 2G12 is a unique cluster of high-mannose type oligosaccharides (oilgomannose) on HIV-1 gp120. Initial mutational studies indicated that the oligomannose sugar chains at the N-glycosylation sites N295, N332, N339, N386, N392, and N448 might be involved in 2G12 recognition (9). Two recent studies further proposed that the epitope of 2G12 might consist of several Manα1-2Man-linked moieties contributed by the oligomannose sugar chains at sites N295, N332, and N392 that form a unique cluster on gp120 (81, 82).

However, HIV-1 gp120 expresses an array of high-mannose oligosaccharides ranging from $Man_5$, $Man_6$, to $Man_9$ on these sites (76-78). These diverse oligomannose glycoforms of the 2G12 epitope on HIV-1 gp120 are likely to dilute any potential immune response to the epitope. This may partially explain why gp120 itself raises a limited number of 2G12-like antibodies. Further, carbohydrates themselves are generally poor immunogens, which may explain why 2G12-like neutralizing antibodies are rare in natural infection. Thus, it would be advantageous to provide a representative carbohydrate structure that would increase production of 2G12 neutralizing antibodies and that could be used as a component in a therapeutic composition.

SUMMARY OF THE INVENTION

The present invention relates to a constructed oligosaccharide cluster, optionally bonded to an immunogenic protein, that can be administered to a subject to induce an immune response for increasing production of neutralizing antibodies, such as 2G12, that bind to a conserved cluster of oligosaccharide sugars on gp120 and/or used in assays as reactive sites for determining compounds that inactivate and/or bind the a conserved cluster of oligosaccharide sugars on gp120.

In one aspect, the present invention relates to at least one high-mannose oligosaccharide positioned on a scaffolding framework or molecule that is conjugated to an immunogenic protein to form a high-mannose oligosaccharide/protein cluster thereby generating an immune enhancing vaccine.

In another aspect, the present invention relates to a novel high-mannose oligosaccharide cluster comprising at least one high-mannose oligosaccharide assembled on a monosaccharide scaffold to provide the first generation of novel, carbohydrate-based HIV-1 vaccine.

In yet another aspect, the present invention relates to a vaccine comprising an oligosaccharide cluster covalently attached to a scaffolding framework, which in turn is conjugated to an immunogenic protein. The general design of such a vaccine is shown in FIG. 2, where $Man_9$ represents the major high-mannose type oligosaccharide structure found on HIV-1 gp120, and the immunogenic protein can be any potent immune-stimulating carrier protein such as KLH (keyhole limpet hemocyanin). The number of the oligosaccharide chains attached to the scaffold could be 2, 3, 4, or more.

Another aspect of the present invention relates to methods for generating an oligosaccharide cluster comprising the steps of:

covalently linking or attaching at least one high-mannose oligosaccharide chain to a scaffold molecule to generate an oligosaccharide cluster that mimics an antigenic structure having affinity for 2G12 antibodies. The high-mannose oligosaccharide chains may be obtained from the digestion of soybean agglutinin or produced by chemical synthesis. High-mannose oligosaccharide chains can include any structural variant of $Man_9$ (containing 9 mannose residues), $Man_8$:, $Man_7$, $Man_6$, $Man_5$ or a combination thereof Any combination of these high-mannose oligosaccharide chains may be attached to a scaffolding framework which may include, but is not limited to, monosaccharides, cyclic peptides, cyclic organic compounds, or compounds such as 11-bis-maleimidetetraethyleneglycol.

In yet another aspect, the present invention relates to antibodies, including polyclonal and monoclonal, and production thereof, wherein the antibody is immunoreactive with an oligosaccharide cluster and/or an oligosaccharide/protein cluster of the present invention.

In still a further aspect, the present invention contemplates a process for producing an antibody, which is immunoreactive with an oligosaccharide cluster and/or an oligosaccharide/protein cluster of the present invention comprising the steps of:

(a) introducing the oligosaccharide cluster and/or the oligosaccharide/protein cluster into a live animal subject; and
(b) recovering antisera comprising antibodies specific for the oligosaccharide cluster and/or the oligosaccharide/protein cluster.

Another aspect relates to a diagnostic testing system for detecting HIV-1 infection, the testing system comprising:

contacting a biological sample being tested for occurrence of HIV-1 virus with antisera specific for a high-mannose oligosaccharide cluster of the present invention that mimics a carbohydrate antigenic structure having affinity for 2G12 antibodies; and determining binding between the antisera and the biological sample.

In another aspect, the present invention contemplates a diagnostic kit for detecting the presence of 2G12 antibodies in a biological sample, wherein the kit comprises a first container containing an oligosaccharide cluster of the present invention capable of immunoreacting with a 2G12 neutralizing antibody in the biological testing sample. Preferably, the kit of the invention further comprises a second container containing a second antibody with an indicator that immunoreacts with a binding antibody to the oligosaccharide cluster of the present invention.

Alternatively, the present invention provides a process for detecting candidate compounds that potentially interact with a conserved cluster of oligomannose sugars on gp120, the process comprising:

contacting the candidate compound with an oligosaccharide cluster and/or an oligosaccharide/protein cluster of the present invention; and
determining the binding affinity of the candidate compound for the oligosaccharide cluster and/or an oligosaccharide/protein cluster of the present invention.

Another aspect of the present invention relates to a method to induce production of neutralizing 2G12 antibodies, the method comprising:

administering to a subject a composition comprising an oligosaccharide cluster and/or an oligosaccharide/protein cluster of the present invention in an effective amount to induce production of neutralizing 2G12 antibodies.

In still another aspect, the present invention relates to a method of treating an HIV-1 virus infection, comprising:

administering to a patient a composition comprising a therapeutically effective amount of the oligosaccharide cluster and/or an oligosaccharide/protein cluster to induce prolonged production of neutralizing antibodies, wherein the neutralizing antibodies have an affinity for a conserved cluster of oligosaccharide sugars on gp120.

Yet another aspect relates to a method of making a high-mannose oligosaccharide/protein cluster comprising the steps of: a) covalently attaching high-mannose oligosaccharides to a scaffolding molecule to form the oligosaccharide cluster; and b) covalently attaching an immunogenic carrier protein to the oligosaccharide cluster to form the high-mannose oligosaccharide/protein cluster.

The high-mannose oligosaccharide/protein cluster of the present invention may be administered alone or in a pharmaceutical composition as a vaccine in a therapeutically effective amount to elicit an enhanced immune response or a protective immune response in an animal.

The compositions of the present invention may further comprise at least one antiviral agent. The antiviral agent may include any agent that inhibits entry into a cell or replication therein of an infectious virus, and specifically retroviruses, such as HIV viruses. The antiviral agents include, but not limited to nucleoside RT inhibitors, CCR5 inhibitors/antagonists, viral entry inhibitors and their functional analogs.

The pharmaceutical compositions may be administered alone or in combination with a therapeutically effective amount of at least one antiviral agent, including, but not limited to:

nucleoside RT inhibitors, such as Zidovudine (ZDV, AZT), Lanivudine (3TC), Stavudine (d4T), Didanosine (ddl), Zalcitabine (ddC), Abacavir (ABC), Emirivine (FTC), Tenofovir (TDF), Delaviradine (DLV), Efavirenz (EFV), Nevirapine (NVP), Fuzeon (T-20), Saquinavir (SQV), Ritonavir (RTV), Indinavir (IDV), Nelfinavir (NFV), Amprenavir (APV), Lopinavir (LPV), Atazanavir, Combivir (ZDV/3TC), Kaletra (RTV/LPV), Trizivir (ZDV/3TC/ABC);

CCR5 inhibitors/antagonists, such as SCH-C, SCH-D, PRO 140, TAK 779, TAK-220, RANTES analogs, AK602, UK-427, 857, monoclonal antibodies;

viral entry inhibitors, such as Fuzeon (T-20), NB-2, NB-64, T-649, T-1249, SCH-C, SCH-D, PRO 140, TAK 779, TAK-220, RANTES analogs, AK602, UK-427, 857; and functional analogs or equivalents thereof.

Yet still another aspect relates to a method of increasing the affinity of epitope mimics of the present invention to gp120 comprising manipulating the spatial orientation of high-mannose oligosaccharide chains on a scaffolding framework to create antibodies exhibiting high-affinity multivalent interaction with a conserved cluster of oligomannose sugars on gp120.

These and other aspects of the present invention, will be apparent from the detailed description of the invention provided hereinafter

Figure 1:
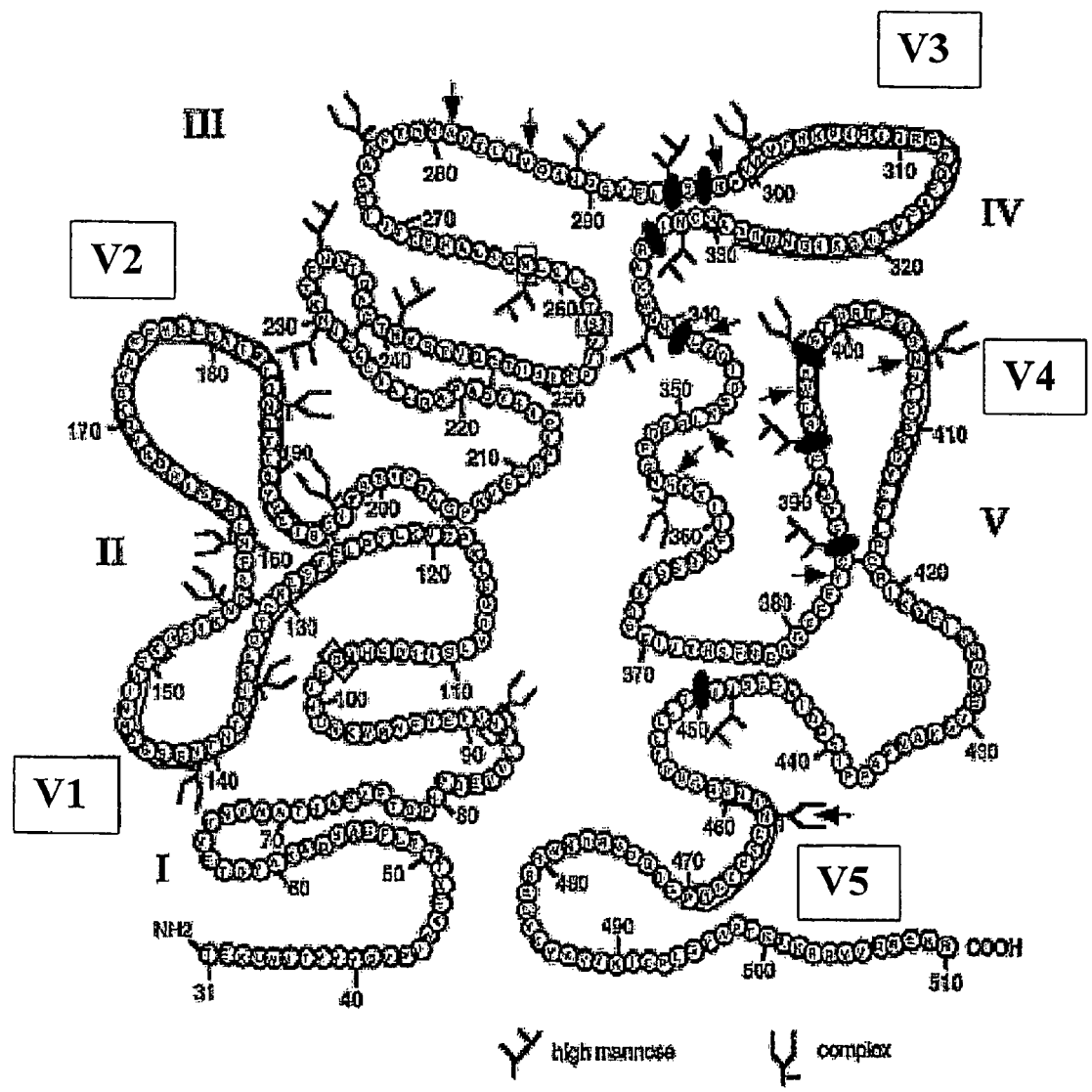
FIG. 1 illustrates Mab 2G12 as described in the prior art by Trkola, et al 1996.

FIG. 16 shows inhibition of 2G12 binding to gp120 by synthetic oligomannose clusters. 2G12 binding (%) was plotted against the log of competing carbohydrate concentrations in micromolar units. Solid diamond, $Man_9GlcNAc_2Asn$; open triangle, $Man_9$-dimer; solid triangle, Bi-$Man_9$; open circle,

DETAILED DESCRIPTION OF THE INVENTION

In order to facilitate review of the various embodiments of the invention and provide an understanding of the various elements and constituents used in making and using the present invention, the following terms used in the invention description have the following meanings.

Definitions

The term "oligosaccharide cluster," as used herein, is a scaffold comprising at least one high-mannose oligosaccharide chain.

The term "oligosaccharide/protein cluster," as used herein means a high-mannose oligosaccharide cluster attached to an immune stimulating carrier protein.

The term "immunogenic protein," as used herein, means a protein suitable for conjugation to the oligosaccharide cluster including, but not limited to keyhole limpet hemocyanin, tetanus toxoid, diphtheria toxoid, bovine serum albumin, ovalbumin, thyroglobulin, myoglobin, cholera toxin β-subunit, immunoglobulin and/or tuberculosis purified protein derivative.

The term "scaffold or scaffolding," as used herein means a structure whereby oligosaccharide chains are attached, wherein the structure may include, but is not limited to monosaccharides, cyclic peptides and/or cyclic organic compounds.

A method of treating a viral infection is meant herein to include "prophylactic" treatment or "therapeutic" treatment. A "prophylactic" treatment is a treatment administered to a subject who does not exhibit signs of a disease or who exhibits early signs of the disease for the purpose of decreasing the risk of developing pathology associated with the disease.

The term "therapeutic," as used herein, means a treatment administered to a subject who exhibits signs of pathology for the purpose of diminishing or eliminating those signs.

The term "therapeutically effective amount," as used herein means an amount of compound that is sufficient to provide a beneficial effect to the subject to which the compound is administered. A beneficial effect means rendering a virus incompetent for replication, inhibition of viral replication, inhibition of infection of a further host cell, or increasing CD4 T-cell count, for example.

The term "specific binding," as used herein, in reference to the interaction of an antibody and a protein or peptide, means that the interaction is dependent upon the presence of a particular structure (i.e., the antigenic determinant or epitope) on the protein; in other words, the antibody is recognizing and binding to a specific protein structure rather than to proteins in general.

As used herein, the term "antibody" refers to intact molecules as well as fragments thereof, such as Fa, $F(ab')_2$, and Fv, which are capable of binding the epitopic determinant.

THE INVENTION

Oligosaccharide Clusters and Oligosaccharide/Immunogenic Protein Clusters

The present invention relates to high-mannose oligosaccharide clusters comprising at least one high-mannose oligosaccharide covalently attached or linked to a scaffold thereby forming a high-mannose oligosaccharide cluster. The high-mannose oligosaccharide is selected from the group consisting of $Man_9$ $Man_8$, $Man_7$, $Man_6$, $Man_5$ and any combination thereof The high-mannose oligosaccharide can be isolated from soybean agglutinin or synthesized by techniques well known to one skilled in the art. Preferably, the scaffold framework comprises at least two high-mannose oligosaccharides, and more preferably, four $Man_9$ are covalently linked to the scaffolding.

The present invention further comprises linking the high-mannose oligosaccharide cluster to an immunogenic protein thereby inducing production of antibodies having an affinity for the high-mannose oligosaccharide cluster. Preferably, the high-mannose oligosaccharide cluster comprises at least two mannose oligosaccharides covalently attached to a monosaccharide scaffold and the oligosaccharide cluster is covalently attached to keyhole limpet hemocyanin acting as the immunogenic protein.

The high-mannose oligosaccharide clusters and oligosaccharide/immunogenic protein clusters of the present invention may be administered as vaccines with various pharmaceutically acceptable carriers. Pharmaceutically acceptable carriers includes those approved for use in animals and humans and include diluents, adjuvants, excipients or any vehicle with which a compound, such as multivalent peptides and/or maleimide clusters, is administered. Pharmaceutically acceptable carriers include but are not limited to water, oils, saline, dextrose solutions, glycerol solutions, excipients such as starch, glucose, lactose, sucrose, gelatin, malt, rice, flour, chalk, silica gel, sodium stearate, glycerol monostearate, talc, sodium chloride, powdered non-fat milk, propylene glycol and ethanol. Pharmaceutical compositions may also include wetting or emulsifying agents, or pH buffering compounds.

It becomes clear that a successful strategy in developing an effective HIV-1 vaccine relies on the identification of conserved epitopes on HIV-1 that are accessible to neutralization and on the design of epitope-based immunogens that stimulate high immune responses. In searching for conserved and accessible antigenic structures for vaccine design, a well known and yet not adequately exploited target, the surface carbohydrate structures of HIV-1 gp120 was selected.

Based on structural analysis, HIV-1 gp120 contains multiple high-mannose type N-glycans. These discontinuous oligosaccharide chains are clustered together to form a unique oligosaccharide microdomain. The high-mannose oligosaccharide cluster has not been found in any glycoproteins and is unique to HIV-1. In addition, recent studies suggest that the high-mannose oligosaccharide cluster may constitute the actual epitopes of the broadly neutralizing 2G12.

Pharmaceutical Compositions

The present invention provides for compositions comprising at least one high-mannose oligosaccharide complex or high-mannose oligosaccharide/protein complex and optionally at least one antiviral agent, as well as methods of enhancing an immune response thereby inducing increased production of neutralizing HIV antibodies for treating and/or reducing the effects of HIV. The methods comprise administering said compositions comprising the one high-mannose oligosaccharide complex or high-mannose oligosaccharide/protein complex and optionally antiviral agents, wherein the two compounds can be administered, separately, simultaneously, concurrently or consecutively.

Anti-Viral Compounds

In one aspect the compositions and methods of the present invention may further comprise a therapeutically effective amount of at least one antiviral agent, including, but not limited to nucleoside RT inhibitors, CCR5 inhibitors/antagonists, viral entry inhibitors and functional analogs thereof.

Preferably, the antiviral agent comprises nucleoside RT inhibitors, such as Zidovudine (ZDV, AZT), Lamivudine (3TC), Stavudine (d4T), Didanosine (ddI), Zalcitabine (ddC), Abacavir (ABC), Emirivine (FTC), Tenofovir (TDF), Delaviradine (DLV), Efavirenz (EFV), Nevirapine (NVP), Fuzeon (T-20), Saquinavir (SQV), Ritonavir (RTV), Indinavir (IDV), Nelfinavir (NFV), Amprenavir (APV), Lopinavir (LPV), Atazanavir, Combivir (ZDV/3TC), Kaletra (RTV/LPV), Trizivir (ZDV/3TC/ABC);

CCR5 inhibitors/antagonists, such as SCH-C, SCH-D, PRO 140, TAK 779, TAK-220, RANTES analogs, AK602, UK-427, 857, monoclonal antibodies;

viral entry inhibitors, such as Fuzeon (T-20), NB-2, NB-64, T-649, T-1249, SCH-C, SCH-D, PRO 140, TAK 779, TAK-220, RANTES analogs, AK602, UK-427, 857; and functional analogs thereof Methods for Preventing and/or Treating a Viral Infection The compositions and methods of the present invention can be used to treat or reduce effects of HIV viral infection in a subject potentially exposed to the infection. At least one high-mannose oligosaccharide complex or high-mannose oligosaccharide/protein complex of the present invention may be administered for the treatment of HIV either as single therapeutic agents or when used in combination with antiretroviral drugs.

A composition of the present invention is typically administered parenterally in dosage unit formulations containing standard, well-known nontoxic physiologically acceptable carriers, adjuvants, and vehicles as desired. The term parenteral as used herein includes intravenous, intramuscular, intraarterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables. Preferred carriers include neutral saline solutions buffered with phosphate, lactate, Tris, and the like.

The compositions of the invention are administered in substantially non-toxic dosage concentrations sufficient to ensure the release of a sufficient dosage unit of the present complexes into the patient to provide the desired inhibition of the HIV virus. The actual dosage administered will be determined by physical and physiological factors such as age, body weight, severity of condition, and/or clinical history of the patient. The active ingredients are ideally administered to achieve in vivo plasma concentrations of an antiviral agent of about 0.01 uM to about 100 uM, more preferably about 0.1 to 10 uM, and most preferably about 1-5 uM, and of a high-mannose oligosaccharide complex or high-mannose oligosaccharide/protein complex of about 1 u.M-25 uM, more preferably about 2-20 uM, and most preferably about 5-10 uM. It will be understood, however, that dosage levels that deviate from the ranges provided may also be suitable in the treatment of a given viral infection.

Therapeutic efficacy of the high-mannose oligosaccharide complexes or high-mannose oligosaccharide/protein complexes can be determined by standard pharmaceutical procedures in cell cultures or experimental animals, e.g., for determining The $LD_{50}$ (The Dose Lethal To 50% Of The Population) and The $ED_{50}$ (the dose therapeutically effective in 50% of the population). The dose ratio between toxic and therapeutic effects is the therapeutic index and it can be expressed as the ratio $LD_{50}/ED_{50}$. Compounds, which exhibit large therapeutic indexes, are preferred. The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Further, the therapeutic compositions according to the present invention may be employed in combination with other-therapeutic agents for the treatment of viral infections or conditions. Examples of such additional therapeutic agents include agents that are effective for the treatment of viral infections or associated conditions such as immunomodulatory agents such as thymosin, ribonucleotide reductase inhibitors such as 2-acetylpyridine 5-[(2-chloroanilino) thiocarbonyl) thiocarbonohydrazone, interferons such as alpha-interferon, 1-beta-D-arabinofuranosyl-5-(1-propynyl)uracil, 3'-azido-3'-deoxythymidine, ribavirin and phosphonoformic acid.

In still another embodiment, the present invention provides antibodies immunoreactive with the high-mannose oligosaccharide complexes or high-mannose oligosaccharide/protein complexes of the present invention. The antibodies may include both monoclonal and polyclonal.

Briefly, a polyclonal antibody is prepared by immunizing an animal with an immunogen comprising a high-mannose oligosaccharide complex or high-mannose oligosaccharide/protein complex of the present invention, and collecting antisera from that immunized animal. A wide range of animal species can be used for the production of antisera. Typically an animal used for production of antisera is a rabbit, a mouse, a rat, a hamster or a guinea pig. Because of the relatively large blood volume of rabbits, a rabbit is a preferred choice for production of polyclonal antibodies.

Exemplary and preferred immunogenic proteins are keyhole limpet hemocyanin (KLH) and bovine serum albumin (BSA). Other albumins such as ovalbumin, mouse serum albumin or rabbit serum albumin can also be used as carriers. Means for conjugating the high-mannose oligosaccharide complex or high-mannose oligosaccharide/protein complex are well known in the art and include glutaraldehyde, M maleimidobenzoyl-N-hydroxysuccinimide ester, carbodiimide and bis-biazotized benzidine.

Immunogenicity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used for the production of polyclonal antibodies varies inter alia, upon the nature of the immunogen as well as the animal used for immunization. A variety of routes can be used to administer the immunogen (subcutaneous, intramuscular, intradermal, intravenous and intraperitoneal). The production of polyclonal antibodies is monitored by sampling blood of the immunized animal at various points following immunization. When a desired level of immunogenicity is obtained, the immunized animal can be bled and the serum isolated and stored.

Typically, a monoclonal antibody of the present invention can be readily prepared by a technique which involves first immunizing a suitable animal with a selected antigen (e.g., the high-mannose oligosaccharide complexes or high-mannose oligosaccharide/protein complexes of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine. This culturing provides a population of hybridomas from which specific hybridomas are selected. Typically, selection of hybridomas is performed by culturing the cells by single-clone dilution in microliter plates, followed by testing the individual clonal supernatants for reactivity with the antigenic oligosaccharide complexes. The selected clones can then be propagated indefinitely to provide the monoclonal antibody.

By way of specific example, to produce an antibody of the present invention, mice are injected intraperitoneally with between about 1-200 ug of an antigen comprising the high-mannose oligosaccharide complex or high-mannose oligosaccharide/protein complex of the present invention. At some time (e.g., at least two weeks) after the first injection, mice are boosted by injection with a second dose of the antigen and optionally mixed with incomplete Freund's adjuvant. A few weeks after the second injection, mice are tail bled and the sera titered by immunoprecipitation against radiolabeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/oligosaccharide complexes of the present invention. Fusion conditions include, for example, the presence of polyethylene glycol. The resulting fused cells are hybridoma cells. Like myeloma cells, hybridoma cells grow indefinitely in culture. Hybridoma cells are separated from unfused myeloma cells by culturing in a selection medium such as HAT media (hypoxanthine, aminopterin, thymidine).

Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media. Each of the surviving hybridoma cells produces a single antibody. These cells are then screened for the production of the specific antibody immunoreactive with an antigen/oligosaccharide complex of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

Screening Assays

In yet another aspect, the present invention contemplates a process of screening substances for their ability to interact with a conserved epitopic cluster of oligosaccharide sugars on gp120 and created mimics of such an epitope including the high-mannose oligosaccharide complexes of the present invention, the process comprising the steps of providing a high-mannose oligosaccharide complex of the present invention and testing the ability of selected test substances to interact with that high-mannose oligosaccharide complexes of the present invention.

The methods of the present invention make it possible to produce large quantities of a high-mannose oligosaccharide complex that mimics an epitope that immunoreacts with Mab 2G12 or antibodies reactive therewith for use in screening assays.

Screening assays of the present invention generally involve determining the ability of a candidate test substance to bind to the high-mannose oligosaccharide complexes of the present invention. These high-mannose oligosaccharide complexes can be coupled to a solid support. The solid support can be agarose beads, polyacrylamide beads, polyacrylic beads or other solid matrices capable of being coupled to proteins. Well known coupling agents include cyanogen bromide, carbonyldiimidazole, tosyl chloride, and glutaraldehyde.

Alternatively, the present invention provides a process of detecting HIV infection, wherein the process comprises immunoreacting the biological samples comprising suspected HIV virus with antibodies generated and having affinity for the high-mannose oligosaccharide complexes of the present invention (mimicking a conserved cluster of oligosaccharide sugars on gp120) to form an antibody-polypeptide conjugate and detecting the conjugates.

A biological sample to be screened can be a biological fluid such as extracellular or intracellular fluid or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide.

In accordance with a screening assay process, a biological sample is exposed to an antibody immunoreactive with the 2G12 epitope located on gp120 of HIV. Typically, the biological sample is exposed to the antibody under biological reaction conditions and for a period of time sufficient for antibody-epitope conjugate formation. Biological reaction conditions include ionic composition and concentration, temperature, pH and the like. Ionic composition and concentration can range from that of distilled water to a 2 molal solution of NaCl. Temperature preferably is from about 25° C. to about 40° C. pH is preferably from about a value of 4.0 to a value of about 9.0, more preferably from about a value of 6.5 to a value of about 8.5 and, even more preferably from about a value of 7.0 to a value of about 7.5. The only limit on biological reaction conditions is that the conditions selected allow for antibody-polypeptide conjugate formation and that the conditions do not adversely affect either the antibody or the peptide.

Exposure time will vary inter alia with the biological conditions used, the concentration of antibody and peptide and the nature of the sample (e.g., fluid or tissue sample). Means for determining exposure time are well known to one of ordinary skill in the art. Typically, where the sample is fluid and the concentration of peptide in that sample is about $10^{-10}$ M, exposure time is from about 10 minutes to about 200 minutes.

The presence of a gp120 in the biological sample is detected by detecting the formation and presence of antibody-peptide conjugates. Means for detecting such antibody-antigen (e.g., peptide) conjugates or complexes are well known in the art and include such procedures as centrifugation, affinity chromatography and the like, binding of a secondary antibody to the antibody-candidate peptide complex.

In one embodiment, detection is accomplished by detecting an indicator affixed to the antibody. Exemplary and well known such indicators include radioactive labels (e.g., $^{32}$P, $^{125}$I, $^{14}$C), a second antibody or an enzyme such as horse radish peroxidase. Means for affixing indicators to antibodies are well known in the art and available in commercial kits.

EXPERIMENTAL PROCEDURES

EXAMPLE 1

The HIV-1 envelope glycoprotein gp120 is important target for HIV-1 vaccine design, although it has been difficult to design effective immunogens that elicit neutralizing antibodies reactive to a broad range of HIV-1 primary isolates (1-3).

In searching for conserved and accessible antigenic structures for vaccine design, attention was turned to the not adequately exploited target, the surface carbohydrate structures of HIV-1 gp120. HIV-1 gp120 contains high numbers of high-mannose type N-glycans, most of which are conserved among HIV-1 isolates. Molecular modeling studies suggest that these otherwise discontinuous carbohydrate moieties are clustered together on folded gp120 to form a unique oligosaccharide microdomain. In addition, the discontinuous epitopes of the broadly neutralizing antibody 2G12 were mapped in the high-mannose N-glycosylation sites.

Figure 2:
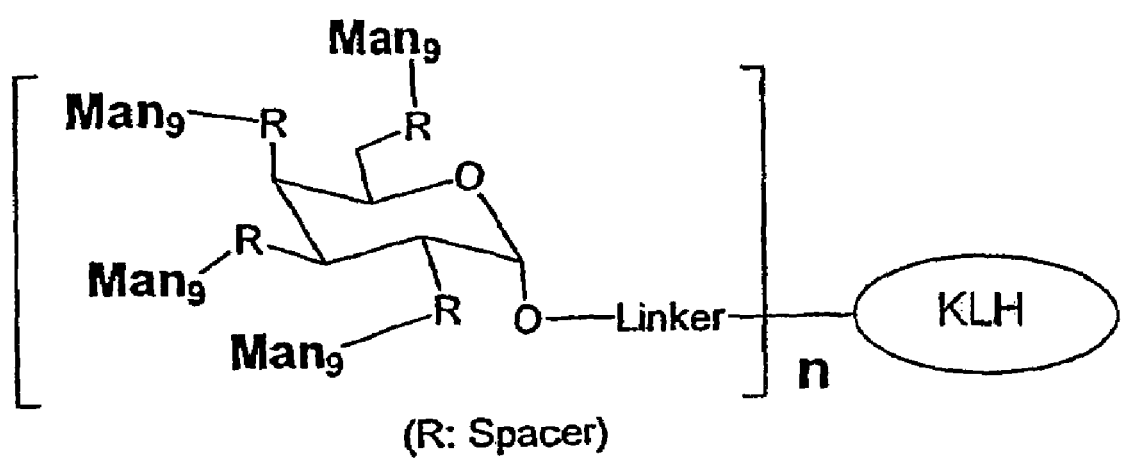
FIG. 2 illustrates the general structure of the conjugate vaccine of the present invention.

The goal of the present invention was to develop an effective anti-HIV vaccine through targeting unique carbohydrate structures present on HIV-1 and incorporating this novel carbohydrate antigenic structure into an HIV-1 vaccine. The general structure of such a vaccine is shown in FIG. 2, where $Man_9$ represents the major high-mannose type oligosaccharide structure found on HIV-1 gp120, and KLH (keyhole limpet hemocyanin) is a potent immune-stimulating carrier protein.

A novel high-mannose oligosaccharide cluster is assembled using a scaffold approach that has been previously used for constructing multivalent peptides (43). As stated above, carbohydrates themselves are generally poor immunogens, which may explain why 2G12-like neutralizing antibodies are rare in natural infection. However, conjugation of the designed carbohydrate antigen to an immunogenic protein such as KLH has the ability to render the designed carbohydrate antigen highly immunogenic.

Carbohydrate-based conjugate vaccines have been developed for eliciting protective immune responses against pathogens such as bacteria (53). However, heretofore carbohydrate antigens have not been adequately exploited for HIV-1 vaccine design, despite their abundance on the HIV-1 surface.

The synthesis of the designed carbohydrate-based conjugate vaccine requires a relatively large quantity of the $Man_9$ oligosaccharides. $Man_9GlcNAc2Asn$ was originally prepared from soybean agglutinin (SBA) through pronase digestion for structural analysis (54, 55). $Man_9GlcNAc_2Asn$ from SBA has been used for chemoenzymatic synthesis of high-mannose type glycopeptides (56, 57). For the purpose of synthesizing the carbohydrate-conjugate vaccine, a modified procedure has been established that allows for the efficient preparation of $Man_9GlcNAc_2Asn$ on a relatively large scale.

Figure 3:
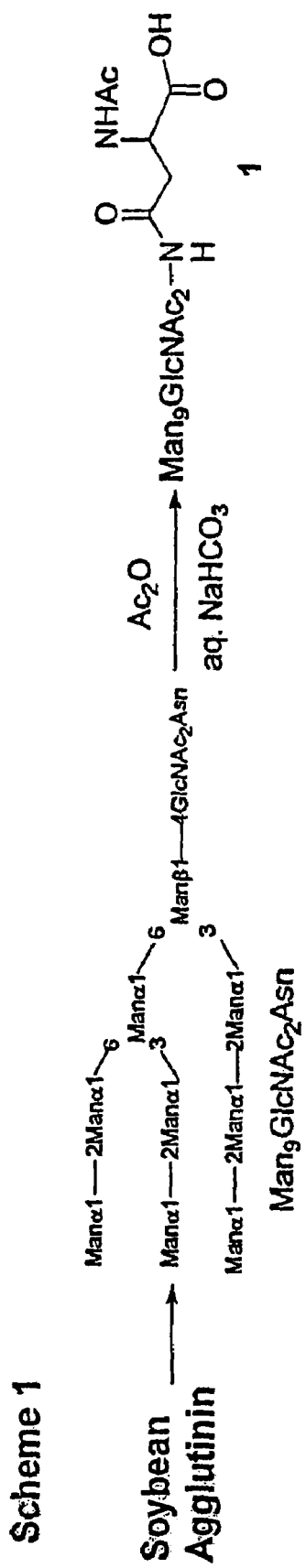
FIG. 3 shows the acetylation of $Man_9GlCNAc_2ASn$.

Crude SBA was obtained by fractional precipitation of non-processed soybean flour (Sigma) with ammonium sulfate (55-65%). The crude SBA was then subject to thorough digestion with pronase (Sigma). High-Performance Anion-Exchange chromatography (HPAEC) with Pulsed Electrochemical Detection (PED) was used to monitor the digestion process. A 48 h digestion led to the conversion of only half of the $Man_9$ oligosaccharide into the form of $Man_9GlcNAc_2Asn$; the rest are in the forms of glycopeptides with several amino acid residues attached, which are relatively difficult to digest. Complete digestion of protein/peptides was achieved through adding extra portions of pronase at intervals and using elongated digestion time (7 days). The final product, $Man_9GlcNAc_2Asn$, was readily isolated by gel filtration chromatography on a column of SEPHADEX G-50 with 0.1 M acetic acid as the eluent. The isolated product was characterized by $^1$H-NMR, ESI-MS, and carbohydrate compositional analysis. From 2 kg of soybean flour, about 180 mg of pure $Man_9GlcNAc_2Asn$ was obtained and the preparation can be readily scaled up. Next, we selectively protected the free amino group of Asn by reacting $Man_9GlcNAc_2Asn$ with acetic anhydride in aqueous sodium bicarbonate to give the acetylated $Man_9GlcNAc_2Asn$ (1) in 85% yield (FIG. 3). Compound 1, with a free carboxyl group in the molecule, is now suitable for coupling to a scaffold to form a clustered high-mannose oligosaccharide structure.

Reliable methods have been established for selective modification of monosaccharides, which have been used as scaffolds (templates) to assemble multivalent gp41 peptides (43). Compared with other scaffold molecules, monosaccharides have a rigid ring structure and allow the display of the antigenic structures in a defined, three-dimensional format. The sugar-scaffold approach is used for the synthesis of the disclosed high-mannose oligosaccharide cluster.

A galactose-based template is synthesized, compound 6, which contains four amino functionalities on the arms that are arranged in a clustered format and are suitable for attachment of four copies of high-mannose oligosaccharide chains. In addition, compound 6 has a carboxyl functionality in the aglycon portion that is used for selective conjugation to a carrier protein (FIG. 4).

Figure 4:
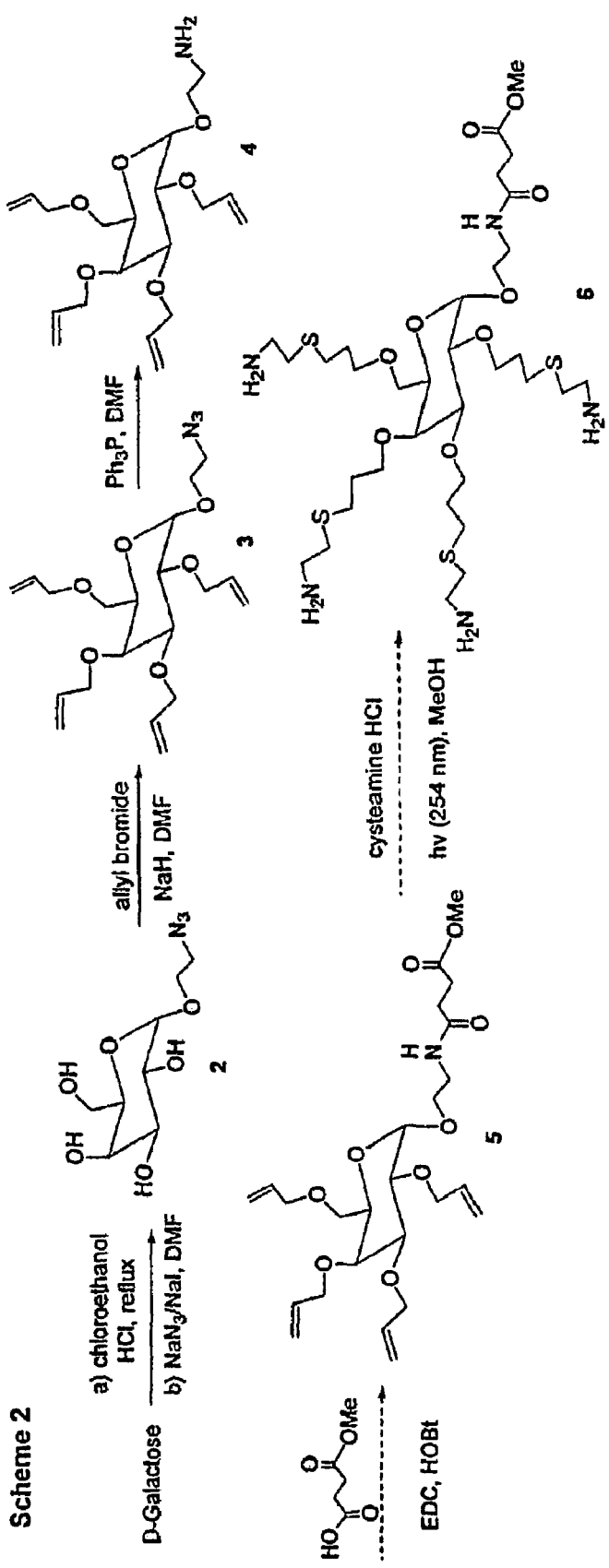
FIG. 4 shows a synthesis scheme of a galactose-based template for attachment of high-mannose oligosaccharide chains.

To prepare compound 6 as shown in FIG. 4, a precursor compound (4) is synthesized. Briefly, an azido functionality was introduced in the aglycon portion of galactose in two steps: 1) refluxing galactose in chloroethanol to form chloroethyl α-galactoside and 2) substitution of the chloro atom with sodium azide to give compound 2 in 78% yield from galactose. Allylation of compound 2 with allyl bromide/NaH in DMF afforded compound 3 in 88% yield. Reduction of the azido group in compound 3 with triphenylphosphine gave compound 4 in 45% yield. All the compounds were purified by silica gel chromatography and characterized by NMR and MS. To complete the synthesis of compound 6, compound 4 is coupled with succinic acid monomethyl ester to provide compound 5. Four amino functionalities are then introduced by photoaddition of cysteamine to the allyl groups to give the template 6 (FIG. 4). Photoaddition of thiols to allyl groups is a very mild reaction for functional group transformations and we have previously used this reaction to prepare cyclodextrin-based polyamines and monosaccharide templates for multivalent peptide assembling (43, 58).

Figure 5:
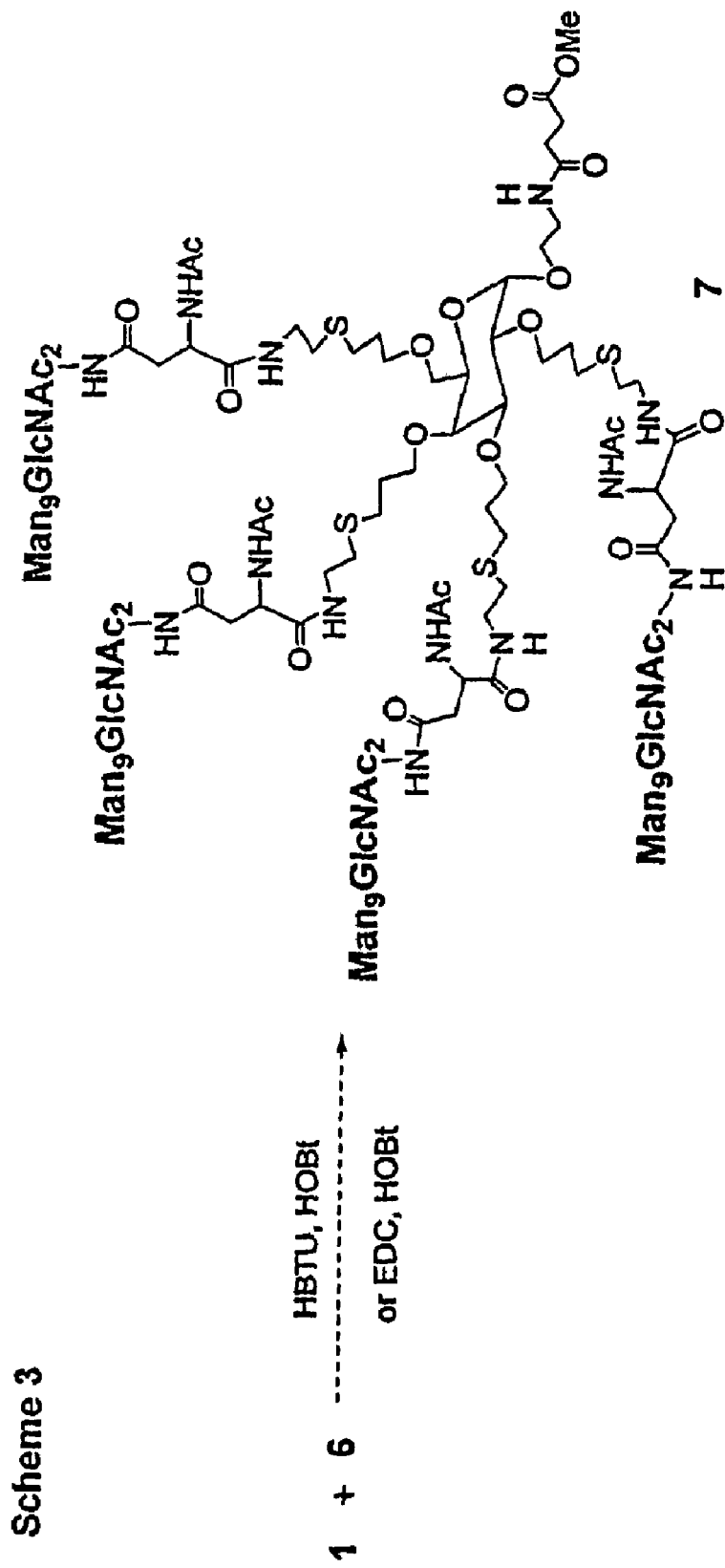
FIG. 5 shows assembly of high-mannose oligosaccharide chains onto a galactose-based template.

Various methods for the coupling of compound 6 with the N-acetylated $Man_9GlcNAc_2Asn$ (1), which is prepared as described for (FIG. 3), are available (FIG. 5). HBTU is used as a coupling reagent. HBTU is a powerful coupling reagent for peptide bond formation and was successfully used for coupling large, unprotected oligosaccharide glycosylamine with carboxyl groups in peptides (59, 60). The coupling reagent such as 1-ethyl-3-(3dimethylaminopropyl) carbodiimide hydrocholoride (EDC) is used to establish optimized conditions for assembly of the cluster. The reactions are monitored using HPLC analysis (reverse phase and size-exclusion).

Figure 6:
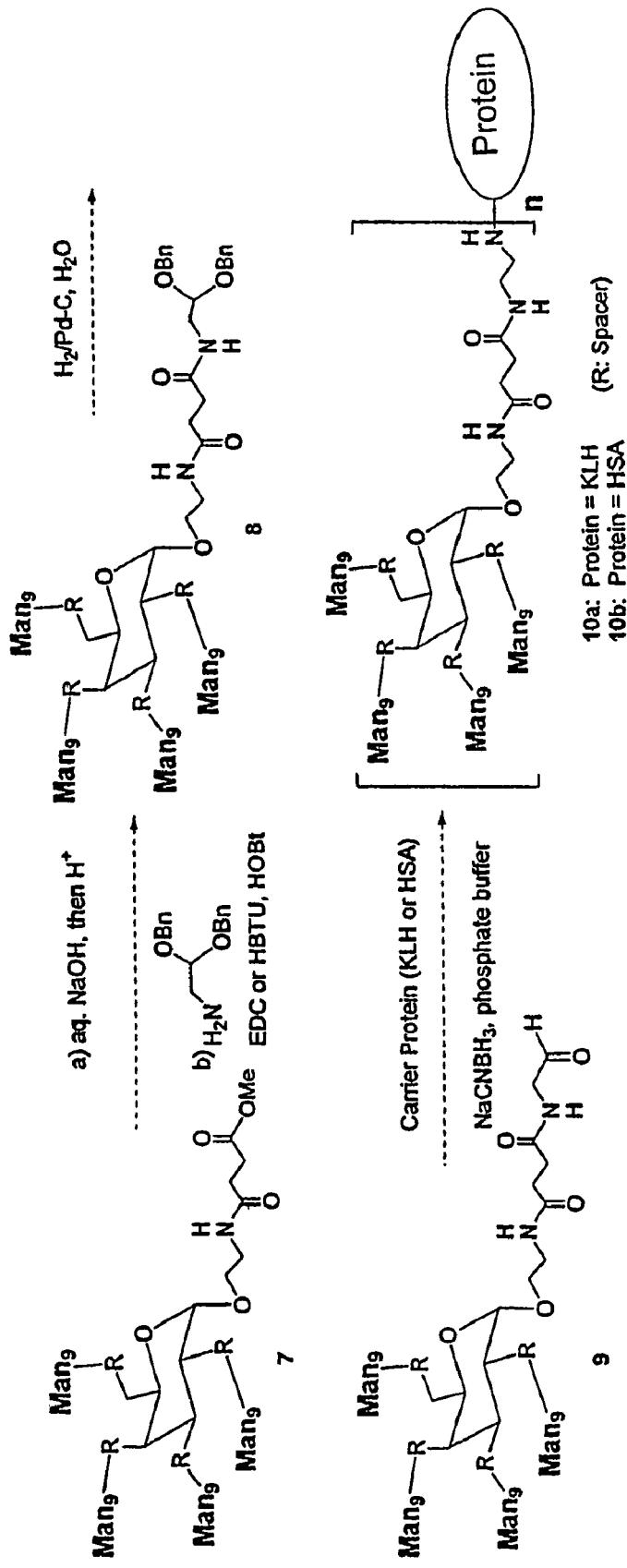
FIG. 6 shows conjugation of the oligosaccharide cluster to a carrier protein.

Conjugation of synthetic carbohydrate antigens to an immune-stimulating carrier protein was accomplished by reductive amination which was shown to be a reliable method for conjugation. Reductive amination is used to conjugate the high-mannose oligosaccharide cluster to KLH. An aldehyde functionality is introduced into the high-mannose oligosaccharide cluster 7. This is achieved through several steps of chemical transformations of 7 (FIG. 6).

First, the ester functionality in compound 7 is hydrolyzed to provide a free carboxylic acid, which is then reacted with 2-aminoacetaldhyde dibenzyl acetal to give compound 8. The benzyl groups in compound 8 are selectively removed by palladium catalyzed hydrogenation to give compound 9, with a free aldehyde functionality in the molecule. Finally reductive amination between compound 9 and KLH is performed with sodium cyanoborohydride (NaCNB113) in a phosphate buffer. The conjugate-vaccine 10a is isolated by dialysis followed by lyophilization. The ratio of antigen to carrier protein is determined by carbohydrate analysis and protein assay. In addition, the coupling of aldehyde 9 to human serum albumin (HSA) is performed in the same way to provide the carbohydrate-HSA conjugate (FIG. 6). Free carbohydrate antigens are difficult to immobilize in ELISA wells because of their very low affinity to plastic surface. The carbohydrate-HSA conjugate 10b is used as a coating antigen for evaluating immune responses in ELISAs.

Figure 7:
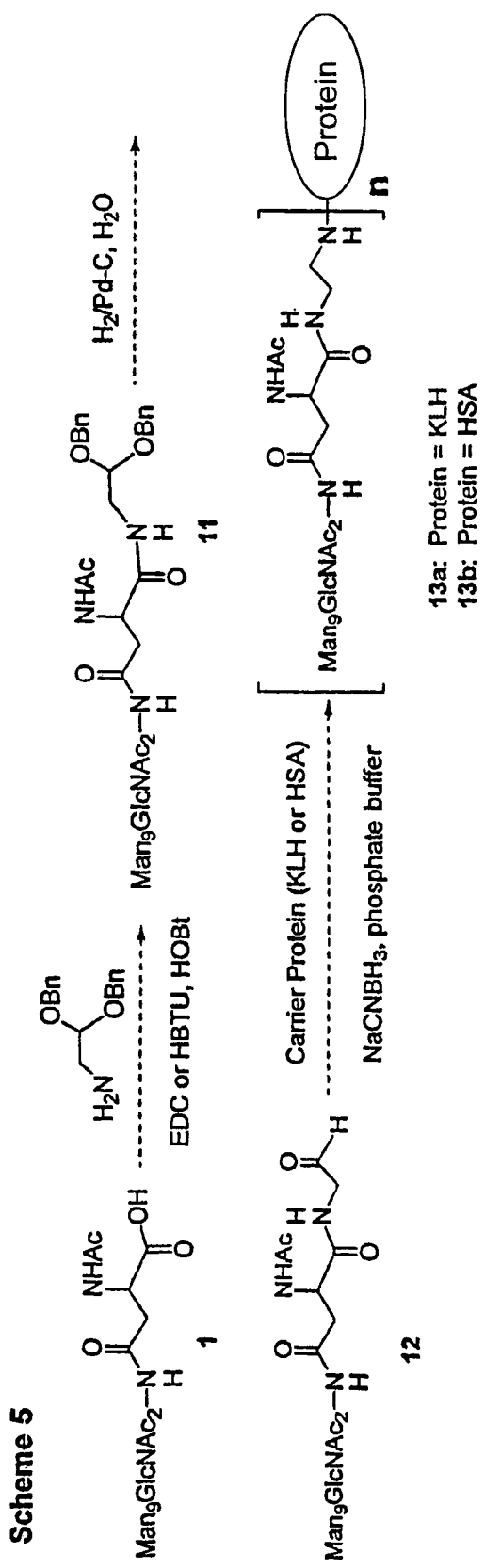
FIG. 7 shows conjugation of a high-mannose oligosaccharide chain to a carrier protein.
Figure 8:
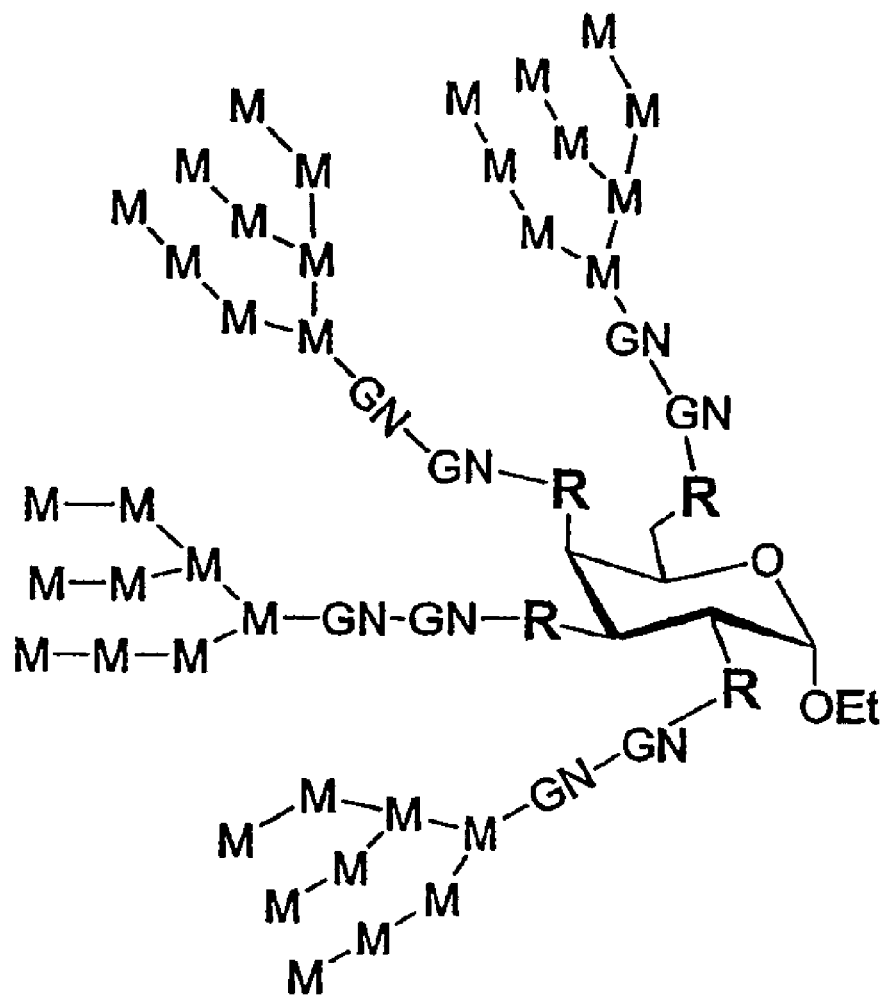
FIG. 8 shows the structure of a high-mannose oligosaccharide cluster.

For comparative studies, a high-mannose oligosaccharide antigen, the N-acetylated $Man_9GlcNAc_2Asn$ (1), is directly conjugated to KLH or HSA (FIG. 7). The aldehyde functional group is introduced into compound 1 in two steps: reaction of compound 1 with 2-aminoacetaldehyde dibenzyl acetal to give compound 11 and subsequent removal of the benzyl groups by hydrogenation to give the aldehyde derivative compound 12. The conjugation of compound 12 to KLH and HSA is performed through reductive amination in the same way as for the preparation of conjugates 10a and 10b, to provide the $Man_9$-KLH conjugate 13a and $Man_9$-HSA conjugate 13b, respectively.

EXAMPLE 2

As a crucial step to include the novel carbohydrate antigen into HIV-1 vaccine design, the high-mannose oligosaccharide cluster is duplicated through chemical synthesis. Assembly of the high-mannose oligosaccharide chains on a suitable scaffold molecule in a defined spatial orientation would provide novel oligosaccharide clusters that mimic or capture the actual structure of the carbohydrate antigen as present on native HIV-1 gp120. A general design of such a clustering antigenic structure is shown in FIG. 1, where four strands of the major HIV-1 high-mannose type oligosaccharide, $Man_9GlcNAc_2$, are presented on a galactoside scaffold. Herein is disclosed an efficient synthesis of the tetravalent high-mannose oligosaccharide cluster and a related bivalent oligosaccharide cluster.

Figure 9:
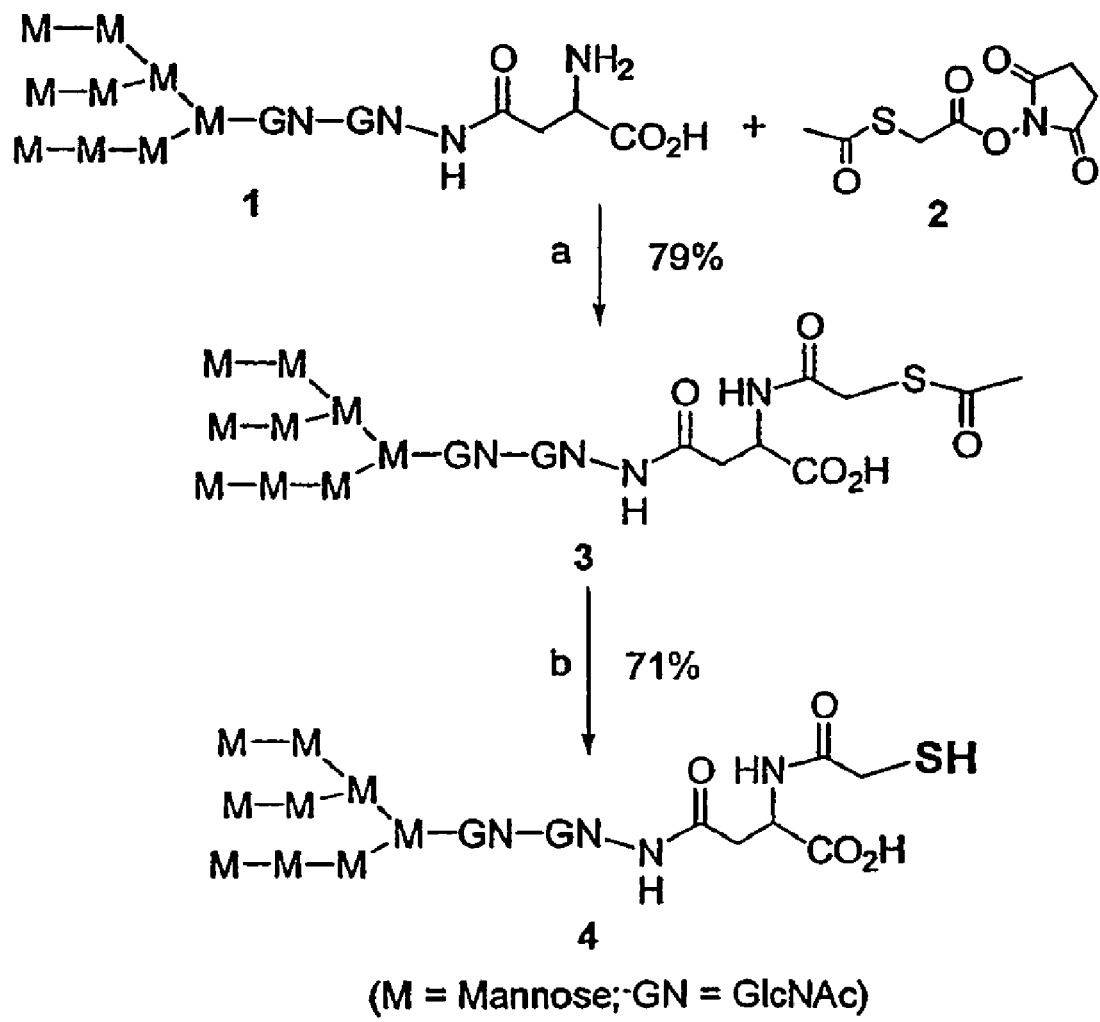
FIG. 9 shows the introduction of a sulfhydryl group onto $Man_9GlcNAc_2Asn$. Reaction conditions: (a) phosphate buffer (pH 7.4) containing 30% MeCN, r.t., 2 h; (b) hydroxylamine (0.5 M), EDTA (25 mM) in phosphate buffer (pH 7.5), r.t., 1 h.

In recent years, many glycol-clusters were synthesized to study the multivalency and clustering effects in carbohydrate-protein interactions (71). But only a few involve the synthesis of glycol-clusters of large oligosaccharide (73). To construct the designed high-mannose oligosaccharide clusters, we took advantage of the highly efficient thiol-maleimide ligation reaction as the key step, which we have recently exploited for the synthesis of very large and complex multivalent peptides (74). The high-mannose type oligosaccharide found on HIV-1, Man$_9$GlcNAc$_2$Asn 1, was prepared through digestion of soybean agglutinin, which was isolated from soybean flour, according to the published method (75). The purified M$_9$GN$_2$Asn was identical to an authentic sample and was further characterized by electrospray ionization mass Spectroscopy (ESI-MS) [1998.73 (M+H)$^+$ 999.69 9M+2H)$^{2+}$, 918.65 (M-Man+2H)$^{2+}$, 837.68 (M-2Man+2H)$^{2+}$, 756.70 (M-3Man+2H)$^{2+}$, 675.52 (M-4Man+2H)$^{2+}$, 594.61 (M-5Man+2H)$^{2+}$). For the ligation as shown in FIG. 9, a sulfhydryl group was successfully introduced into the oligosaccharide in two steps (Scheme 1). First, the amino group in Man$_9$GlcNAc$_2$Asn (1) was selectively acylated with N-succinimidyl S-acetylthioacetate (SATS)$^{75}$ in a phosphate buffer (pH 7.4) containing 30% acetonitrile to give the N—(S-acetyl-thioacetyl) derivative (3) [ESI-MS: 2114.55 (M+H)$^+$, 1057.66 (M+2H)$^{2+}$, 976.55 (M-Man+2H)$^{2+}$, 895.45 (M-2Man+2H)$^{2+}$, 815.54 (M-3Man+2H)$^{2+}$, 733.43 (M-4Man+2H)$^{2+}$, 652.39 (M-5Man+2HI)$^{2+}$, 571.34 (M-6Man+2H)$^{2+}$]. As shown in FIG. 9, the thiol-protective group in compound 3 was then removed by treatment with hydroxylamine in a phosphate buffer (pH 7.5) to afford the thiol compound 4, which was purified by HPLC and characterized by ESI-MS [2072.56 (M+H)$^+$, 1036.71 (M+2H)$^{2+}$, 955.68 (M-Man+2H)$^{2+}$, 874.71 (M-2Man+2H)$^{2+}$, 793.66 (M-3Man+2H)$^{2+}$, 712.56 (M-4Man+2H)$^{2+}$, 631~51 (M-5Man+2H)$^{2+}$, 550.66 (M-6Man+2H)$^{2+}$]. The oligosaccharide derivative 4, which contains a sulfhydryl tag at the reducing terminus, is an important intermediate for synthesizing useful glycol-clusters of high-mannose type oligosaccharides.

Figure 10:
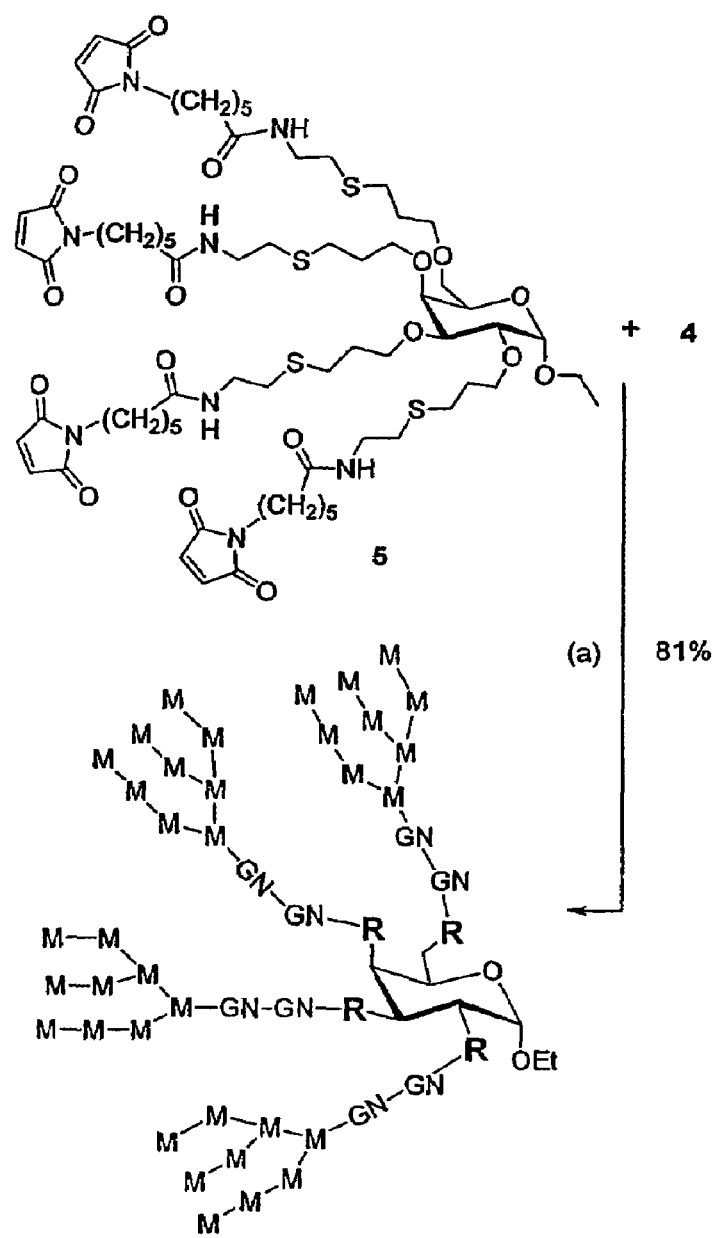
FIG. 10 shows ligation between the maleimide cluster 5 and the thiol oligosaccharide derivative 4. Reaction conditions: (a) phosphate buffer (pH 6.6, 50 mM) containing 40% MeCN, r.t., 1 h.
Figure 10:
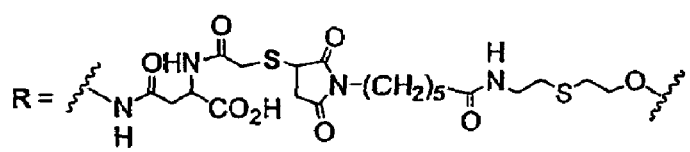

A galactoside-based, tetravalent maleimide cluster 5 had been previously synthesized (73). The ligation between the maleimide cluster 5 and the thiol 4 was performed in a phosphate buffer (pH 6.6) containing 40% acetonitrile to afford the desired tetravalent oligosaccharide cluster 6 (Scheme 2). Briefly, procedures for the preparation of the oligosaccharide cluster 6 are as follows. To a solution of thiol 4 ((7.60 mg, 3.67 umol) in a phosphate buffer (pH, 6.6, 50 mM, 1.2 ml) was added a solution of the galactose-based maleimide cluster 5 (shown in FIG. 10)(0.67 mg, 0.46 umol) in acetonitrile (0.8 ml). The mixture was kept at room temperature under nitrogen atmosphere. After 1 h. The mixture was lyophilized. The residue was purified by reverse-phase HPLC to afford the tetravalent high-mannose oligosaccharide cluster 6 (3.60 mg, 81%). The purified product appeared as a single peak at 16.10 min under the following analytical HPLC conditions: column, Waters Nova-Pak C18 (3.9×150 mm); temperature, 40° C.; flow rate, 1 ml/min. The column was eluted with a linear gradient of acetonitrile (0-50%) containing 0.1% TFA in 25 min.

HPLC revealed that the ligation was quantitative and was complete within 1 h at room temperature. A simple HPLC purification gave the tetravalent high-mannose type oligosaccharide cluster 6 in 81% isolated yield. The ESI-MS and HPLC profile of compound 6 was shown in FIG. 12. Typical fragments of compound 6 in ESI-MS are 2435.35 (M+4H)$^{4+}$, 2394.95 (M-Man+4H)$^{4+}$, 1948.28 (M+5H)$^{5+}$, 1915.85 (M-Man+5H)$^{5+}$, and 1883.75 (M-2Man+5H)$^{5+}$, which are in agreement with its structure.

Figure 11:
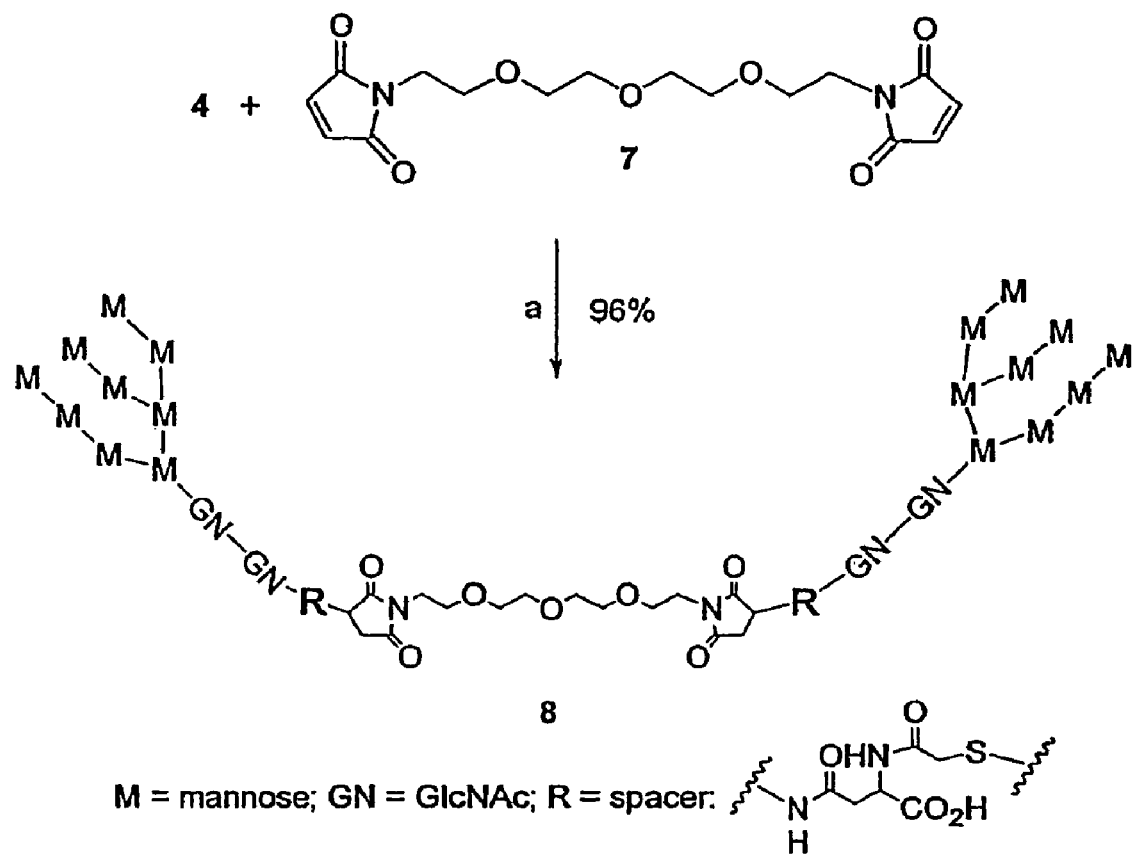
FIG. 11 shows ligation between the bivalent scaffold 7 and the thiol oligosaccharide derivative 4. Reaction conditions: (a) phosphate buffer (pH 6.6), r.t., 1 h.

The synthetic approach should be equally efficient for constructing an array of different oligosaccharide clusters on varied monosaccharides or other scaffolds. As another example, we synthesized a bivalent high-mannose oligosaccharide cluster 3 that will be useful for comparative binding studies with the antibody 2G12. Thus, ligation of the thiol 4 and a bivalent scaffold 11-bis-maleimidetetraethyleneglycol BM(PBO)$_4$)(7) shown in FIG. 11, gave the bivalent oligosaccharide cluster 8 in essentially quantitative yield. Compound 8 was purified by HPLC and characterized by ESI-MS [2248.78 (M+2H)$^{2+}$, 1499A9 (M+3H)$^{3+}$, 1445.45 (M-Man+3H)$^{3+}$, 1391.28 (M-2Man+3H)$^{3+}$, 1337.44 (M-3Man+3H)$^{3+}$, 1283.27 (M-4Man+3H)$^{3}$].

In summary, an efficient route for the construction of glycol-clusters involving large, native oligosaccharides is disclosed. The approach consists of two key steps: selective introduction of a SH-tag into the oligosaccharide and a chemoselective ligation of the SH-tagged oligosaccharide with a maleimide cluster. The ligation reaction is rapid, highly efficient, and essentially quantitative even when very large oligosaccharides are involved. A galactose-based, tetravalent high-mannose type oligosaccharide cluster (in which four strands of the oligosaccharide are arranged in a defined spatial orientation on the galactose scaffold has been synthesized. The tetravalent oligosaccharide cluster provides a direct mimic to the carbohydrate epitope of the broadly HIV-1 neutralizing antibody 2G12.

EXAMPLE 3

Methods and Materials

Materials:

Monosaccharides, pronase, Sephadex, trifluoroacetic acid, and reagents for ELISAs and buffers were purchased from Sigma-Aldrich and used as received. N-succinimidyl S-acetylthioacetate was from Pierce Chemical Co. HPLC grade acetonitrile was purchased from Fisher Scientific. The immobilized endo-β-N-acetyl-glucosaminidase from *Arthrobactor* (Endo-A) was overproduced and purified according to the literature (79).

High-performance liquid chromatography (HPLC): Unless otherwise specified, analytical HPLC was carried out on a Waters 626 HPLC instrument under the following conditions: column, Waters Nova-Pak C18 (3.9×150 mm); temperature, 40° C.; flow rate, 1 ml/min. The column was eluted with a linear gradient of acetonitrile (0-50%) containing 0.1% TFA in 25 min with UV detection at 214 nm. Preparative HPLC was performed on a Waters 600 HPLC instrument with a preparative C18 column (Waters Symmetry 300, 19×300 mm). The column was eluted with a suitable gradient of water-acetonitrile containing 0.1% TFA.

High-Performance Anion Exchange Chromatography Coupled with Pulsed Electrochemical Detection (HPAEC-PED):

The analytical anion-exchange chromatography was performed on a Dionex DX600 chromatography system (Dionex Corporation, Sunnyvale, Calif.) equipped with an electrochemical detector (ED50, Dionex Corporation, Sunnyvale, Calif.). The following conditions were used: column, Carbo-Pac-PA1 (4×250 mm); Eluent A, 0.1 M NaOH; Eluent B, 1 M sodium acetate (NaOAc) in 0.1 M NaOH; Gradient: 0-5 min, 0% B; 5-25 min, 0-15% B. Flow rate, 1 ml/min.

Competitive Enzyme-Linked Immunosorbent Assays (ELISAs):

Competitive ELISAs were performed to determine the relative inhibition potency of various carbohydrate antigens against the binding of 2G12 to gp120. Microtiter plates were coated with human cell line 293-expressed HIV-1$_{IIIB}$ gp120 (100 ng/ml) overnight at 4° C. After washing, non-specific binding was blocked with 5% BSA in PBS for 1 h at room temperature. The plates were then washed three times with 0.1% Tween-20/PBS. Serial dilutions (1:2) of various carbohydrate antigens were mixed with an equal volume of MAb 2G12 (fixed final concentration of 5 ng/ml) and added to the plates. The plates were incubated for 1 h at 37° C. and washed with washing buffer. To the plates was added a 100-µl solution of 1:3000 diluted horseradish peroxidase-conjugated goat anti-human IgG in 0.5% BSA/PBS. After incubation for 1 h at 37° C., the plates were washed again and a 100-µl solution of 3,3',5,5'-tetramethyl benzidine (TMB) was added. Color was allowed to develop for 5 min, and the color reaction was quenched through adding a 100-µl solution of 0.5 M $H_2SO_4$ to each well. The optical density was then measured at 450 nm.

Preparation of Homogeneous High-Mannose Type Oligosaccharides.

$Man_9GlcNAc_2Asn$ and $Man_9GlcNAc$ were prepared by enzymatic digestion of soybean agglutinin followed by chromatographic purification. Crude soybean agglutinin (3.2 g) was obtained from 500 g of soybean flour (Sigma) through fractional precipitation with ammonium sulfate and digested thoroughly with pronase (2×15 mg, Sigma) according to the literature (74). The digestion was filtered and the filtrate was lyophilized. The residue was loaded onto a column (1.5×70 cm) of Sephadex G50 (Sigma), which was pre-equilibrated and eluted with 0.1M AcOH.

The fractions containing $Man_9GlcNAc_2Asn$ were pooled and lyophilized. The material was finally purified by reverse-phase HPLC to afford homogeneous $Man_9GlcNAc_2Asn$ (55 mg) as a white powder after lyophilization. Treatment of $Man_9GlcNAc_2Asn$ (20 mg) with immobilized *Arthrobactor* endo-β-N-acetylglucosaminidase (Endo-A) in an acetate buffer (pH 6.0), followed by gel filtration on a column (1.5× 50 cm) of Sephadex G25 gave pure $Man_9GlcNAc$ (12 mg).

Homogeneous $Man_5GlcNAc$ and $Man_6GlcNAc$ were obtained from pronase digestion of chicken ovalbumin followed by chromatographic purification. Chicken ovalbumin (Sigma) was digested with pronase to provide a crude mixture of $Man_5$- and $Man_6$-containing glycopeptides, according to the literature (80). A crude glycopeptide (350 mg) was treated with immobilized Endo-A to release $Man_5GlcNAc$ and $Man_6GlcNAc$ as a mixture. The two oligosaccharides were then separated by chromatography on a column (1×125 cm) of Celite-Charcoal (1:1, w/w), which was eluted by a gradient of 0-20% aqueous ethanol to give pure $Man_5GlcNAc$ (25 mg) and pure $Man_6GlcNAc$ (30 mg). The purity of the above isolated oligosaccharides was confirmed by HPAEC-PED and their identity was characterized by electron spray ionization mass spectrometry (ESI-MS).

$Man_9GlcNAc_2Asn$: HPAEC-PED, $t_R$ 17.1 min; ESI-MS: calcd. for $C_{74}H_{124}N_4O_{58}$: 1997.77. Found: 1998.73 $(M+H)^+$, 999.69 $(M+2H)^{2+}$, 918.65 $(M-Man+2H)^{2+}$, 837.68 $(M-2Man+2H)^{2+}$, 756.70 $(M-3Man+2H)^{2+}$, 675.52 $(M-4Man+2H)^{2+}$, 594.61 $(M-5Man+2H)^{2+}$.

$Man_9GlcNAc$: HPAEC-PED, $t_R$ 16.9 min; ESI-MS, calcd. for $C_{62}H_{105}NO_{51}$: 1679.57. Found: 1680.80 $(M+H)^+$, 1518.64 $(M-Man+H)^+$, 1356.72 $(M-2Man+H)^+$, 1194.54 $(M-3Man+H)^+$, 1032.60 $(M-4Man+H)^+$, 841.36 $(M+2H)^{2+}$.

$Man_6GlcNAc$: HPAEC-PED, $t_R$ 15.9 min; ESI-MS, calcd. for $C_{44}H_{75}NO_{36}$: 1193.41. Found: 1216.84 $(M+Na)^+$, 1194.81 $(M+H)^+$, 608.99 $(M+2Na)^{2+}$.

$Man_5GlcNAc$: HPAEC-PED, $t_R$ 15.3 min; ESI-MS, calcd. for $C_{38}H_{65}NO_{31}$: 1031.35. Found: 1054.70 $(M+Na)^+$, 1032.79 $(M+H)^+$, 528.07 $(M+2Na)^{2+}$.

Preparation of the SH-Tagged $Man_9$ Oligosaccharide ($Man_9GlcNAc_2Asn$-Ac-SH).

To a solution of $Man_9GlcNAc_2Asn$ (32 mg) in a phosphate buffer (3 ml, pH 7.4) containing 20% acetonitrile was added a solution of N-succinimidyl S-acetylthioacetate (20)(22 mg) in acetonitrile (0.5 ml). The mixture was stirred at room temperature for 1 h and lyophilized. The product was purified by reverse phase-HPLC to give the N—(S-acetyl-thioacetyl) Man9GlcNAc2Asn derivative (26 mg): analytical HPLC (gradient: 0-30% acetonitrile containing 0.1% TFA in 25 min; flow rate, 1 ml/min): $t_R$ 6.3 min; ESI-MS: 2114.55 $(M+H)^+$, 1057.66 $(M+2H)^{2+}$, 976.55 $(M-Man+2H)^{2+}$, 895.45 $(M-2Man+2H)^{2+}$, 815.54 $(M-3Man+2H)^{2+}$, 733.43 $(M-4Man+2H)^{2+}$, 652.39 $(M-5Man+2H)^{2+}$, 571.34 $(M-6Man+2H)^{2+}$].

A solution of the N—(S-acetyl-thioacetyl) derivative (20 mg) in a phosphate buffer (2 ml, 50 mM, pH 7.4) containing hydroxylamine (50 mM) was stirred at room temperature for 2 h, and the De-S-acetylated product was directly purified by reverse phase HPLC to give the SH-tagged oligosaccharide $Man_9GlcNAc_2Asn$-Ac-SH (15 mg), which was characterized by HPLC and ESI-MS. Analytical HPLC (gradient: 0-30% acetonitrile containing 0.1% TFA in 25 min, flow rate, 1 ml/min): $t_R$ 2.7 min; ESI-MS: 2072.56 $(M+H)^+$, 1036.71 $(M+2H)^{2+}$, 955.68 $(M-Man+2H)^{2+}$, 874.71 $(M-2Man+2H)^{2+}$, 793.66 $(M-3Man+2H)^{2+}$, 712.56 $(M-4Man+2H)^{2+}$, 631.51 $(M5Man+2H)^{2+}$, 550.66 $(M-6Man+2H)^{2+}$.

Synthesis of Tetravalent Oligomannose Cluster (Tetra-$Man_9$).

To a solution of $Man_9GlcNAc_2Asn$-Ac-SH (7.60 mg, 3.67 µmol) in a phosphate buffer (pH, 6.6, 50 mM, 1.2 ml) was added a solution of the galactose-based maleimide cluster MC-1 (0.67 mg, 0.46 µmol) in acetonitrile (0.8 ml). The mixture was gently shaken at room temperature under nitrogen atmosphere for 1 h. The mixture was then lyophilized. The ligation product was purified by reverse-phase HPLC to afford Tetra-$Man_9$ (3.60 mg, 81%). Analytical HPLC: $t_R$, 16.1 min; ESI-MS: 2435.35 $(M+4H)^{4+}$, 2395.15 $(M-Man+4H)^{4+}$, 1948.28 $(M+5H)^{5+}$, 1915.85 $(M-Man+5H)^{5+}$, and 1883.75 $(M-2Man+5H)^{5+}$, which are in agreement with its structure.

Synthesis of Trivalent Oligomannose Cluster (Tri-$Man_9$).

The trivalent maleimide cluster MC-3 (1.0 mg) and $Man_9GlcNAc_2Asn$-Ac-SH (8.0 mg) were reacted in the same way as for the preparation of Tetra-$Man_9$. The ligation product was purified by reverse-phase HPLC to give the Tri-$Man_9$ (7.3 mg, 82%). Analytical HPLC, $t_R$, 15.5 min; ESI-MS: 2457.90 $(M+3H)^{3+}$, 1843.64 $(M+4H)^{4+}$, 1802.92 $(M-Man+4H)^{4+}$, 1762.68 $(M-2Man+4H)^{4+}$, 1722.10 $(M-3Man+4H)^{4+}$, 1681.79 $(M-4Man+4H)^{4+}$.

Synthesis of Bivalent Oligomannose Cluster (Bi-$Man_9$).

The bivalent maleimide cluster MC-2 (1.3 mg) and $Man_9GlcNAc_2Asn$-Ac-SH (9.4 mg) were reacted in the same way as for the preparation of Tetra-$Man_9$. The ligation product was purified by reverse-phase HPLC to give the Bi-$Man_9$ (6.1 mg, 80%). Analytical HPLC, $t_R$, 15.4 min; ES-MS: 2502.12 $(M+2H)^{2+}$, 1668.22 $(M+3H)^{3+}$, 1614.19 $(M-Man+3H)^{3+}$, 1560.24 $(M-2Man+3H)^{3+}$, 1506.01 $(M-3Man+3H)^{3+}$, 1452.54 $(M-4Man+3H)^{3+}$.

Preparation of $Man_9$-dimer $Man_9GlcNAc_2Asn$-Ac-SH (8 mg) was dissolved in a phosphate buffer (2 ml, 50 mM, pH 7.5) and air was bubbled into the solution for 10 min. The solution was kept at room temperature overnight. The oxidized product thus formed was purified by reverse phase HPLC to give the $Man_9$-dimer (5.6 mg). Analytical HPLC (gradient: 0-30% acetonitrile containing 0.1% TFA in 25 min, flow rate, 1 ml/min): $t_R$ 5.3 min; ESI-MS: 2072.0 $(M+2H)^{2+}$, 1381.6 $(M+3H)^{3+}$, 1327.5 $(M-Man+3H)^{3+}$, 1273.4 $(M-2Man+3H)^{3+}$, 1219.45 $(M-3Man+3H)^{3+}$, 1165.41 $(M-4Man+3H)^{3+}$, 1111.2 $(M-5Man+3H)^{3+}$.

Binding of Homogeneous High-Mannose Type Oligosaccharides to 2G12

Figure 13:
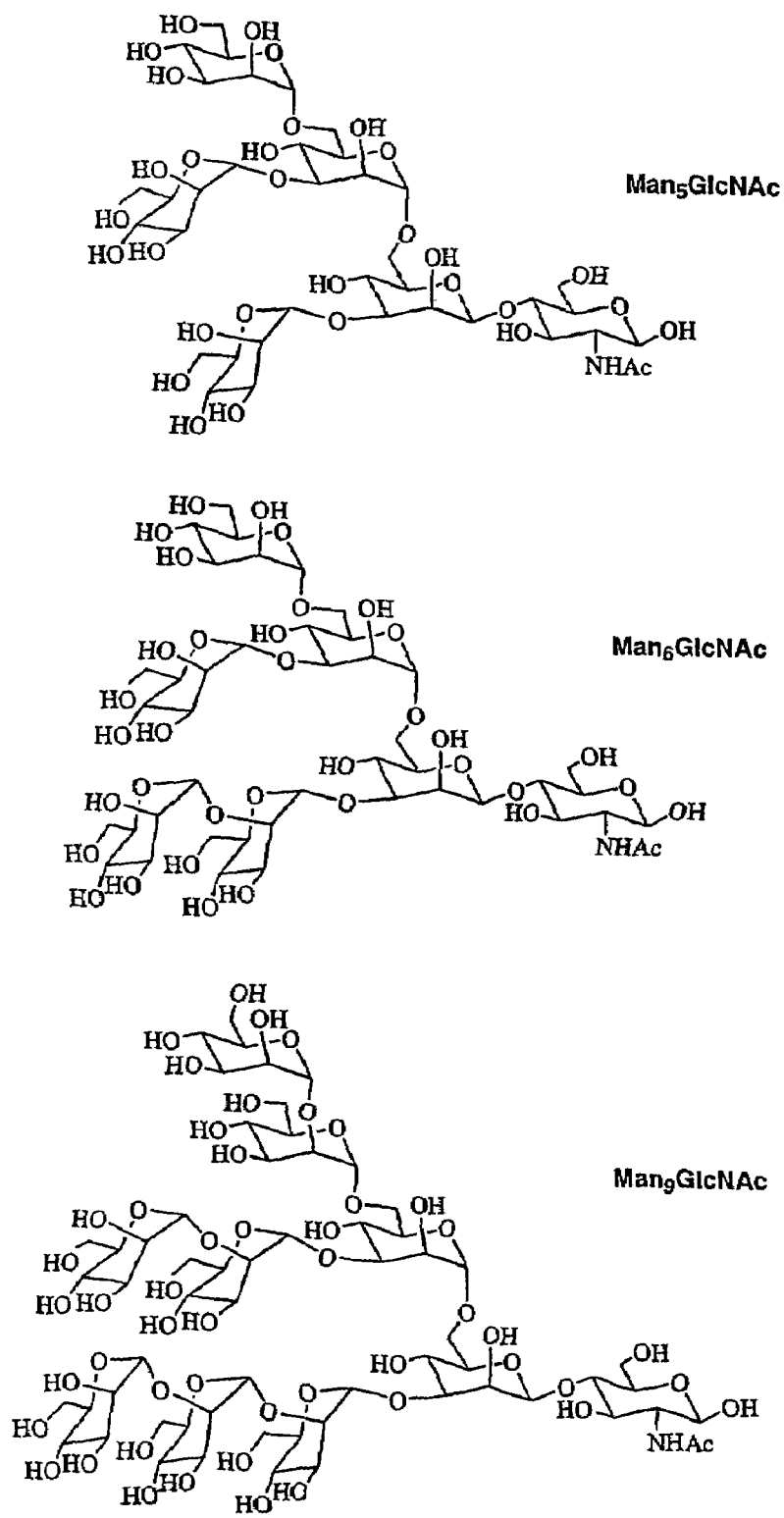
FIG. 13 shows structures of typical HIV-1 high-mannose oligosaccharides.

Structural analysis indicated that the high-mannose type oligosaccharides on HIV-1 gp120 are heterogeneous, ranging from $Man_5$, $Man_6$, $Man_7$, $Man_8$, to $Man_9$ (81-83). However, isolation of individual high-mannose oligosaccharides directly from HIV-1 gp120 is technically difficult. To evaluate the affinity of each glycoform in 2G12 interaction, we isolated three typical high-mannose type oligosaccharides, namely $Man_5GlcNAc$, $Man_6GlcNAc$, and $Man_9GlcNAc$, as shown in FIG. 13 in high-purity from chicken ovalbumin and soybean agglutinin, respectively. The mixture of $Man_5GlcNAc$ and $Man_6GlcNAc$ obtained by sequential treatment of chicken ovalbumin with pronase and *Arthrobactor* endo-β-N-acetylglucosaminidase (Endo-A) was carefully separated on a Celite-Carbon chromatography to afford each oligosaccharide. Based on HPAEC-PED analysis, the $Man_5GlcNAc$ and $Man_6GlcNAc$ thus isolated are at least 98% pure without cross contamination (data not shown). Similarly, ultra-pure $Man_9GlcNAc$ was obtained through sequential digestion of soybean agglutinin with pronase and Endo-A, followed by gel filtration on Sephadex G25 and reverse phase HPLC purification.

Figure 14:
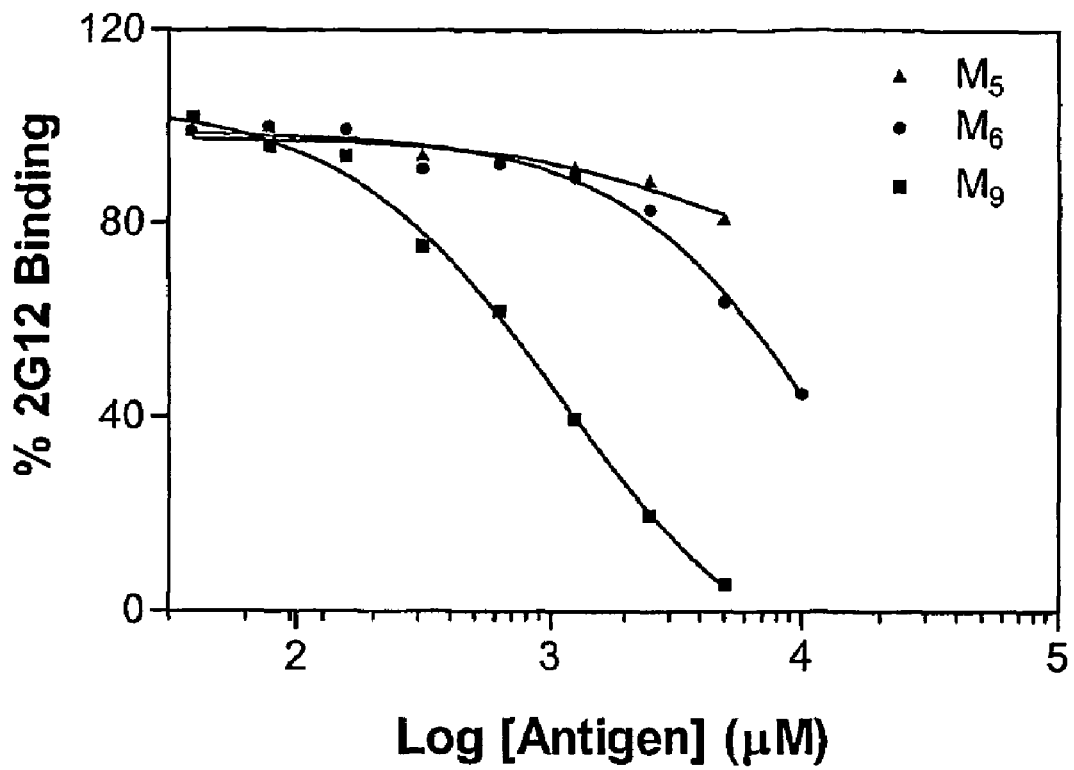
FIG. 14 shows inhibition of 2G12 binding to gp120 by high-mannose type oligosaccharides of the present invention. 2G12 binding (%) was plotted against the log of competing carbohydrate concentrations in micromolar units. Triangle, $Man_5GlcNAc$; solid circle, $Man_6GlcNAc$; solid square, $Man_9GlcNAc$.

The binding affinity of the high-mannose oligosaccharides was examined by competitive inhibition of 2G12 binding to immobilized gp120, as shown in FIG. 14. The IC50 (concentration for 50% inhibition) for $Man_9GlcNAc$, $Man_6GlcNAc$, and $Man_5GlcNAc$ were estimated to be 0.85, 70, and 200 mM, respectively. It should be pointed out that the solubility of $Man_5GlCNAc$ and $Man_6GlcNAc$ in aqueous solution is unexpectedly low (less than 80 mM). As a result, the IC50 for $Man_5GlcNAc$ and $Man_6GlcNAc$ could not be accurately determined. On a molar basis, the $Man_9GlcNAc$ was 85-fold and 244-fold more effective in inhibition of 2G12 binding than $Man_6GlcNAc$ and $Man_5GlcNAc$, respectively. These results suggest that antibody 2G12 preferably recognizes $Man_9$ moiety among the oligomannose glycoforms on HIV-1 gp120. The much higher affinity of $Man_9GlcNAc$ to 2G12 than that of $Man_5GlcNAc$ and $Man_6GlcNAc$ implicates the importance of terminal Manα1,2Man linkages in antibody recognition. In comparison, $Man_9GlcNAc$ contains three terminal Manα1,2Man linkages, $Man_6GlcNAc$ contains one Manα1,2Man linkage, but $Man_5GlcNAc$ does not have any terminal Manα1,2Man linkage. The results are consistent with previous observation that the Manα1,2Man moiety on HIV-1 gp120 is an essential component of 2G12 epitope, as revealed by the binding of various glycosidase-treated gp120 with 2G12 (83).

Design and Synthesis of Oligomannose Clusters as Mimics of 2G12 Epitope

Figure 15:
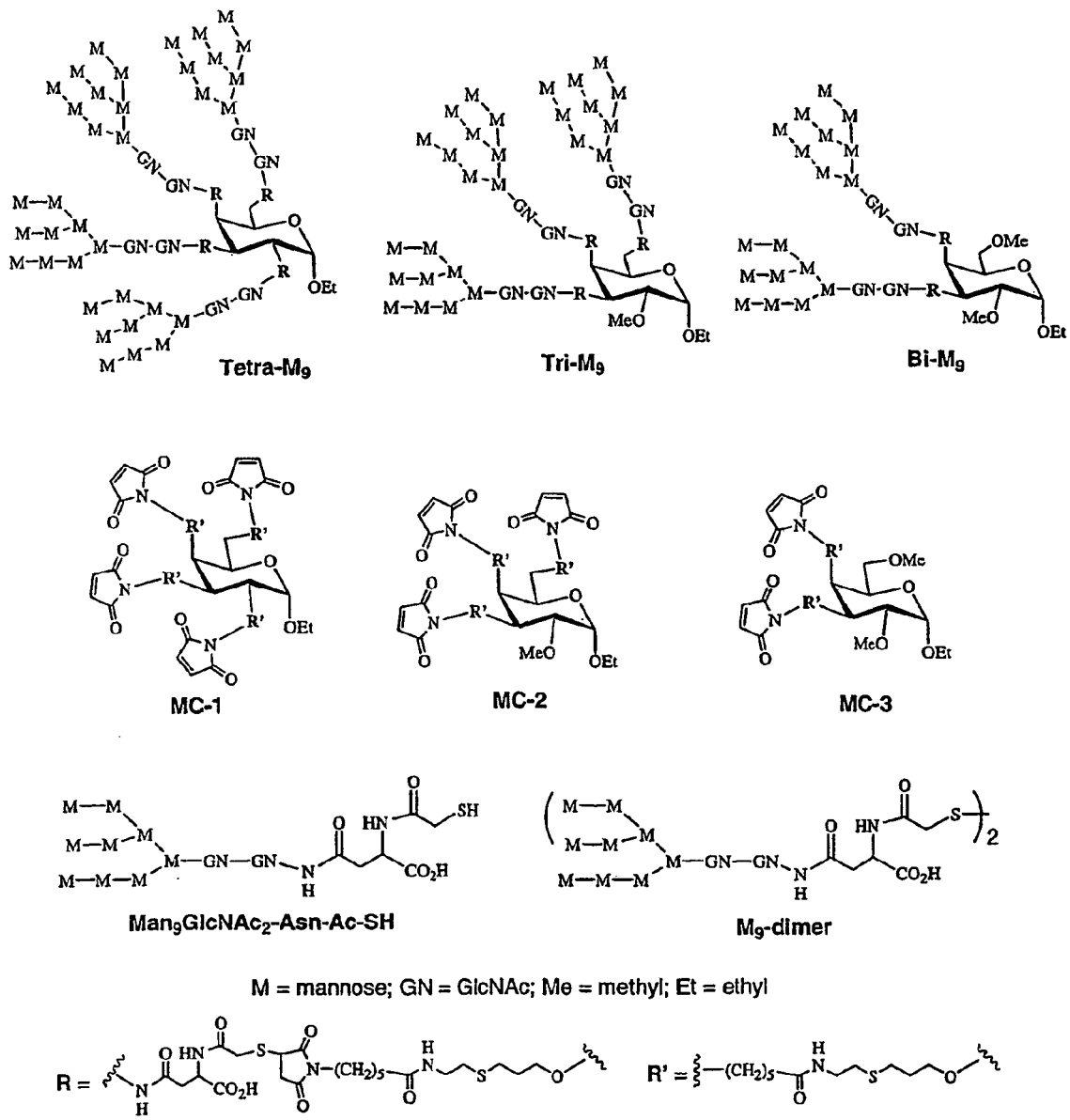
FIG. 15 shows structures of galactose-based maleimide clusters and synthetic oligomannose clusters.

The binding studies with homogeneous high-mannose type oligosaccharides demonstrated that the $Man_9$ subunit is preferred for 2G12 recognition. As an important step to incorporate the novel epitope into HIV-1 vaccine design, the proposed oligomannose cluster was duplicated through chemical synthesis. The assembly of oligomannose such as $Man_9$ on a suitable scaffold molecule was generated to provide oligosaccharide clusters that may mimic or capture 2G12 epitope as present on HIV-1 gp120. Bi-, tri- and tetra-valent $Man_9$ clusters were synthesized based on a galactopyranoside scaffold as shown in FIG. 15. Compared to other types of molecules, monosaccharides have several advantages to serve as a scaffold. They have a rigid ring structure, possess multiple functionalities, and provide a defined three-dimensional spatial arrangement of substituents. When a galactopyranoside is used as the scaffold to present the oligosaccharides, the oligosaccharide chains being installed at C-3, 4, and 6 positions will face up above the sugar ring to form a cluster, while the oligomannose sugar chain at position C-2 is likely to be located on the flank of the cluster. This arrangement was determined to mimic the spatial orientation of the carbohydrate epitope of antibody 2G12. Based on the reported structure (21) of gp120 core with remodeled N-glycans, the distances between the asparagines (Asn) side chains of the pairs N295-N332, N332-N392, and N295-N392 are estimated to be 5.8, 20.3, and 23.6 Å, respectively. A $Man_9GlcNAc_2Asn$ moiety was positioned on a synthesized galactose-based maleimide cluster previously synthesized by the current inventor (83). It was found that the maleimide cluster can host four $Man_9GlcNAc_2Asn$ moieties, in which the distances among the Asn residues are in the range of 8-30 Å (data not shown).

Figure 12:
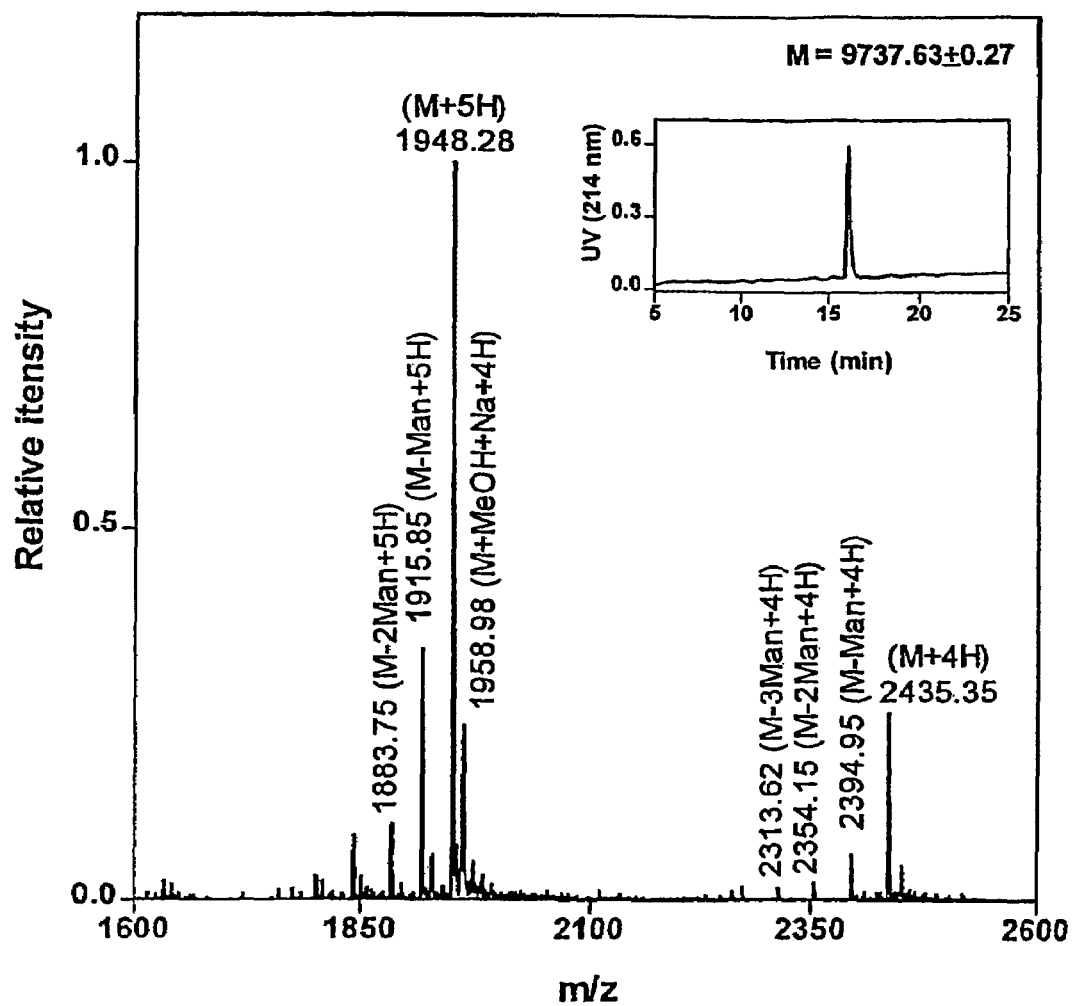
FIG. 12 shows ESI-MS and HPLC profile of the tetra-Man9 cluster (i.e., Tetra-Man9, as shown in FIG. 15).

The key step in the synthesis is the chemoselective, maleimide cluster-thiol ligation reaction, which was recently exploited for the synthesis of large multivalent peptides and glycoconjugates (83-84). To introduce a sulfhydryl (SH)-tag into the oligomannose moiety, the free amino group in $Man_9GlcNAc_2Asn$ was first acylated with N-succinimidyl S-acetylthioacetate (SATS)(86) to give the N—(S-acetylthioacetyl) derivative. The S-acetyl group was then removed selectively by treatment with hydroxylamine to afford the SH-containing oligosaccharide, $Man_9GlcNAc_2Asn$-Ac-SH. The synthesis of the tetravalent maleimide cluster MC-1 was previously reported. The bi- and tri-valent maleimide cluster MC-2 and MC-3 were synthesized in a similar way starting with modified galactoside scaffold (Details of the synthesis will be reported elsewhere). Chemoselective ligation between the $Man_9GlcNAc_2Asn$-Ac-SH and the maleimide cluster MC-1 was performed in a phosphate buffer (pH 6.6). HPLC monitoring indicated that the ligation was quantitative and was complete within 1 h at room temperature. Simple reverse phase HPLC purification gave the tetravalent oligomannose cluster Tetra-$Man_9$ in 81% yield. The structure of Tetra-$Man_9$ was characterized by electron spray ionization-mass spectroscopy (ESI-MS) (FIG. 12). The ESI-MS spectrum revealed typical signals at 2435.35 $(M+4H)^{4+}$, 2395.15 $(M-Man+4H)^{4+}$, 1948.28 $(M+5H)^{5+}$, 1915.85 $(M-Man+5H)^{5+}$, and 1883.7 $(M-2Man+5H)^{5+}$, which are in agreement with the structure.

Similarly, the bi- and trivalent $Man_9$ clusters, Bi-$Man_9$ and Tri-$Man_9$, were synthesized through ligation of $Man_9GlcNAc_2Asn$-Ac-SH with the maleimide clusters MC-2 and MC-3, respectively. On the other hand, a dimmer of $Man_9GlcNAc_2Asn$ was prepared through oxidation of $Man_9GlcNAc_2Asn$-Ac-SH to give the $Man_9$-dimer (FIG. 15). All the final products were purified by HPLC to homogeneity and characterized by ESI-MS.

Binding of the Synthetic $Man_9$-clusters to 2G12

Figure 16:
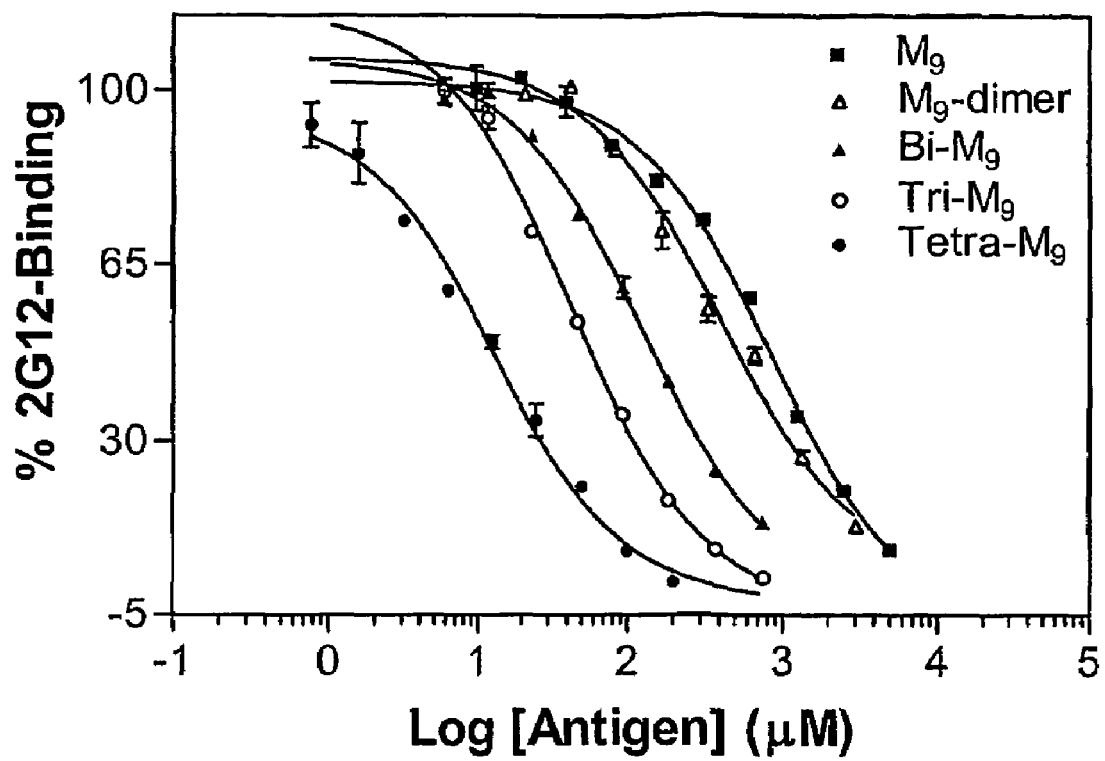

The synthetic $Man_9$-clusters were examined for competitive inhibition of 2G12 binding to immobilized gp120 (FIG. 16). A significant clustering effect was observed for the $Man_9$-clusters as shown in Table 1 below.

Potency on carbohydrate inhibition of 2G12 binding to gp120

| Carbohydrate antigens | IC 50 (nM) | Relative Affinity | |
|---|---|---|---|
| | | Molar basis | Valency-corrected |
| Man$_5$GlcNAc | 200 estimated | 0.004 | 0.004 |
| Man$_6$GlcNAc | 70 | 0.012 | 0.012 |
| Man$_9$GlcNAc | 0.98 | 0.84 | 0.84 |
| Man$_9$GlcNAc2Asn | 0.82 | 1.0 | 1.0 |
| Man9-dimer | 0.40 | 2.1 | 1.0 |
| Bi-Man9 | 0.13 | 6.3 | 3.2 |
| Tri-Man9 | 0.044 | 18.6 | 6.2 |
| Tetra-Man9 | 0.013 | 63.1 | 15.8 |

If IC$_{50}$ is taken as an indication for relative affinity (Table 1), the Tetra-Man$_9$ was found to inhibit the 2G12 binding 63-fold more effectively than monomeric Man$_9$GlcNAc$_2$Asn does on a molar basis. This corresponds to a 16-fold increase in the affinity to 2G12 for each oligosaccharide subunit in Tetra-Man$_9$ on a valence-corrected basis, when compared with monomeric Man$_9$. On the other hand, the trivalent cluster Tri-Man$_9$ was 19-fold (on a molar basis) or 6-fold (on a valence-corrected basis) more effective than Man$_9$GlcNAc$_2$Asn in inhibition of 2G12 binding to gp120. Interestingly, for the two bivalent oligosaccharides Bi-Man$_9$ and Man$_9$-dimer, they showed significantly different affinity toward 2G12. The Man$_9$-dimer inhibited the 2G12-binding 2-fold more effectively than Man$_9$GlcNAc$_2$Asn, while the Bi-Man$_9$ was 6-fold better than Man$_9$. This suggests that the geometry and the distance between the two oligomannose subunits are important factors in controlling antibody recognition. It was also found that the subunit Man$_9$GlcNAc and Man$_9$GlcNAc$_2$Asn showed essentially the same affinity for 2G12 binding. The data suggest that the GlcNAc-Asn moiety linking the oligosaccharide to the protein is not directly involved in the recognition with 2G12. The observation could not be revealed through mutagenesis studies.

The 2G12 binding studies demonstrated that Man$_9$GlNAc is 85- and 244-fold more effective than Man$_6$GlcNAc and Man$_5$GlcNAc, respectively, in inhibition of 2G12 binding to gp120. Therefore, oligomannose Man$_9$ should be the "building block" of choice for creating mimics of 2G12's epitope. The established scaffold approach of the present invention allows efficient synthesis of template-assembled oligosaccharide clusters, in which the oligomannose sugar chains are presented in a defined three-dimensional fashion. Thus, bi-, tri-, and tetra-valent oligomannose clusters were efficiently constructed on a galactose scaffold, using the chemoselective maleimide cluster-thiol ligation as the key step.

An apparent clustering effect of the oligomannose clusters was observed in the inhibition studies. The tetra-, tri-, and bi-valent oligomannose clusters are 63-, 19-, and 6-fold more effectively than the monomeric Man$_9$GlcNAc$_2$Asn in inhibition of 2G12 binding to gp120 on a molar basis. The enhanced affinity for the clusters with higher valency suggests that antibody 2G12 may have multiple binding sites for the carbohydrate antigen. The observed enhancement in 2G12 binding for the higher-valent oligomannose clusters is consistent with the existence of additional binding sites on 2G12 for carbohydrate antigen. Another interesting finding in the above reported binding studies came from the two bivalent oligomannose compounds, Bi-Man$_9$ and Man$_9$-dimer. They showed significantly different binding potency to 2G12 despite the same valency. The Bi-Man$_9$ is 3-fold more effective than Man$_9$-dimer in inhibition of 2G12 binding to gp120. The results suggest that the control of geometry and distance of the subunits is important to achieve a tight multivalent interaction between the carbohydrate antigen and the antibody. As such modification and manipulation of the spatial orientation of oligomannose sugar chains on the scaffold provides for improved epitope mimics and increase affinity of gp120 to the epitope mimics relative to 2G12.

REFERENCES

All publications mentioned herein are hereby incorporated by reference herein for the all purposes.

1. Mascola, J. R.; Snyder, S. W.; Weislow, O. S.; Belay, S. M.; Belshe, R. B.; Schwartz, D. H.; Clements, M. L.; Dolin, R.; Graham, B. S.; Gorse, G. J.; Keefer, M. C.; McElrath, M. J.; Walker, M. C.; Wagner, K. F.; McNeil, J. G.; MeCutchan, F. E.; Burke, D. S. Immunization with envelope subunit vaccine products elicits neutralizing antibodies against laboratory-adapted but not primary isolates of human immunodeficiency virus type 1. *J Infect Dies* 1996, 173, 340-348.
2. Alcott, T. C.; Betake, F. R.; Burke, D. S.; Redfield, R. R.; Bird, D. L. Lack of induction of antibodies specific for conserved, discontinuous epitopes of HIV-1 envelope glycoprotein by candidate AIDS vaccines. *J Immunol* 1995, 155, 4100-4110.
3. Schwartz, D. H.; Gorse, G.; Clements, M. L.; Belshe, R.; Izu, A.; Duliege, A. M.; Berman, P.; Twaddell, T.; Stablein, D.; Sposto, R.; et al. Induction of HIV-1-neutralizing and syncytium-inhibiting antibodies in uninfected recipients of HIV-1IIIB rgp120 subunit vaccine. *Lancet* 1993, 342, 69-73.
4. Burton, D. R. A vaccine for HIV type 1: the antibody perspective. *Proc Natl Acad Sci USA* 1997, 94, 10018-10023.
5. Wyatt, R.; Sodroski, J. The HIV-1 envelope glycoproteins: fusogens, antigens, and immunogens. *Science* 1998, 280, 1884-1888.
6. Sattentan, Q. J.; Moulard, M.; Brivet, B.; Botto, F.; Guillemot, J. C.; Mondor, I.; Poignard, P.; Ugolini, S. Antibody neutralization of HIV-1 and the potential for vaccine design. *Immunol Lett.* 1999, 66, 143-149.
7. Nabel, G. J.; Challenges and opportunities for development of an AIDS vaccine. *Nature* 2001, 410, 1002-1007.
8. Burton, D. R.; Pyati, J.; Koduri, R.; Sharp, S. J.; Thornton, O. B.; Parren, P. W.; Sawyer, L. S.; Hendry, R. M.; Dunlop, N.; Nara, P. L.; et al. Efficient neutralization of primary isolates of HIV-1 by a recombinant human monoclonal antibody. *Science* 1994, 266, 1024-1027.
9. Trkola, A.; Purtscher, M.; Muster, T.; Ballaun, C.; Buchacher, A.; Sullivan, N.; Srinivasan, K.; Sodroski, J.; Moore, J. P.; Katinger, H.; Human monoclonal antibody 2G12 defines a distinctive neutralization epitope on the gp120 glycoprotein of human immunodeficiency virus type 1. *J Virol* 1996, 70, 1100-1108.
10. Conley, A. J.; Kessler, 3. A., 2nd; Boots, L. J.; Tung, J. S.; Arnold, B. A.; Keller, P. M.; Shaw, A. R.; Emini, E. A. Neutralization of divergent human immunodeficiency virus type I variants and primary isolates by IAM-41-2F5, an anti-gp41 human monoclonal antibody. *Proc. Natl. Acad Sci. U & A.* 1994, 91, 3348-3352.
11. Zwick, M. B.; Labrijn, A. F.; Wang, M.; Speniehauer, C.; Saphire, E. O.; Binley, J. M.; Moore, J. P.; Stiegler, G.; Katinger, H.; Burton, D. R.; Parren, P. W. Broadly neutralizing antibodies targeted to the membrane-proximal external region of human immunodeficiency virus type 1 glycoprotein gp41. *J Virol* 2001, 75, 10892-10905.

12. Mascola, J. R.; Stiegler, G.; VanCott, T. C.; Katinger, H.; Carpenter, C. B.; Hanson, C. E.; Beary, H.; Hayes, D.; Frankel, S. S.; Birx, D. L.; Lewis, M. G.; Protection of macaques against vaginal transmission of a pathogenic HIV-1/SIV chimeric virus by passive infusion of neutralizing antibodies. *Nat Med* 2000, 6, 207-210.

13. Baba, T. W.; Liska, V.; Hofmann-Lehmann, R.; Vlasak, J.; Xu, W.; Ayehunie, S.; Cavacini, L. A.; Posner, M. R.; Katinger, H.; Stiegler, G.; Bernacky, B. J.; Rizvi, T. A.; Schmidt, R.; Hill, L. R.; Keeling, M. E.; Lu, Y.; Wright, J. E.; Chou, T. C.; Ruprecht, R. M. Human neutralizing monoclonal antibodies of the IgG1 subtype protect against mucosal simian-human immunodeficiency virus infection. *Nat Med* 2000, 6, 200-206.

14. DeVico, A.; Silver, A.; Thronton, A. M.; Sarngadhran, M. G.; Pal, R. Covalently crosslinked complexes of human immunodeficiency virus type I (HIV-1) gp120 and CD4 receptor elicit a neutralizing immune response that includes antibodies selective for primary virus isolates. *Virology* 1996, 218, 258-263.

15. LaCasse, R. A.; Follis, K. E.; Trahey, M.; Scarborough, J. D.; Littman, D. R.; Nunberg, J. H. Fusion-competent vaccines: broad neutralization of primary isolates of HIV. *Science* 1999, 283, 357-362.

16. Leonard, C. K.; Spellman, M. W.; Riddle, L.; Harris, R. J.; Thomas, J. N.; Gregory, T. J. Assignment of intrachain disulfide bonds and characterization of potential glycosylation sites of the type 1 recombinant human immunodeficiency virus envelope glycoprotein (gp120) expressed in Chinese hamster ovary cells. *J Biol Chem* 1990, 265, 10373-10382:

17. Mizuochi, T.; Matthews, T. J.; Kato, M.; Hamako, J.; Titani, K.; Solomon, J.; Feizi, T. Diversity of oligosaccharide structures on the envelope glycoprotein gp120 of human immunodeficiency virus 1 from the lymphoblastoid cell line H9. Presence of complex-type oligosaccharides with bisecting N-acetylglucosamine residues. *J Biol Chem* 1990, 265, 8519-8524.

18. Geyer, H.; Holschbach, C.; Hunsmann, G.; Schneider, J. Carbohydrates of human immunodeficiency virus. Structures of oligosaccharides linked to the envelope glycoprotein 120. *J Biol Chem* 1988, 263, 11760-11767.

19. Zhu, X.; Borchers, C.; Bienstock, R. J.; Tomer, K. B. Mass spectrometric characterization of the glycosylation pattern of HIV-gp120 expressed in CHO cells. *Biochemistry* 2000, 39, 11194-11204.

20. Kwong, P. D.; Wyatt, R.; Robinson, J.; Sweet, R. W.; Sodroski, J.; Hendrickson, W. A. Structure of an HIV gp120 envelope glycoprotein in complex with the CD4 receptor and a neutralizing human antibody. *Nature* 1998, 393, 648-659.

21. Wyatt, R.; Kwong, P. D.; Desjardins, E.; Sweet, R. W.; Robinson, J.; Hendrickson, W. A.; Sodroski, J. G. The antigenic structure of the HIV gp120 envelope glycoprotein. *Nature* 1998, 393, 705-711.

22. Gerencer, M.; Barrett, P. N.; Kistner, O.; Mitterer, A.; Dorner, F. Natural IgM antibodies in baby rabbit serum bind high-mannose glycans on HIV type I glycoprotein 120/160 and activate classic complement pathway. *AIDS Res Hum Retroviruses* 1998, 14, 599-605.

23. Arendrup, M.; Sonnerborg, A.; Svennerholm, B.; Akerblom, L.; Nielsen, C.; Clausen, H.; Olofsson, S.; Nielsen, J. O.; Hansen, J. E. Neutralizing antibody response during human immunodeficiency virus type 1 infection: type and group specificity and viral escape. *J Gen Virol* 1993, 74, 855-863.

24. Hansen, J. E.; Nielsen, C.; Clausen, H.; Mathiesen, L. R; Nielsen, J. O. Effect of anti-carbohydrate antibodies on HIV infection in a monocytic cell line (U937). *Antiviral Res* 1991, 16, 233-242.

25. Tomiyama, T.; Lake, D.; Masuho, Y.; Hersh, E. M. Recognition of human immunodeficiency virus glycoproteins by natural anti-carbohydrate antibodies in human serum; *Biochem Biophys Res Commun* 1991, 177, 279-285.

26. Cunto-Amesty, G.; Dam, T. K.; Luo, P.; Monzavi-Karbassi, B.; Brewer, C. F.; Van Cott, T. C.; Kieber-Emmons, T. Directing The immune response to carbohydrate antigens. *J Biol Chem* 2001, 276, 30490-30498.

27. Ezekowitz, R. A.; Kuhlman, M.; Groopman, J. E.; Bym, R. A. A human serum mannose-binding protein inhibits in vitro infection by tile human immunodeficiency virus. *J Exp Med* 1989, 169, 185-196.

28. Hansen, J. E.; Nielsen, C. M.; Nielsen, C.; Heegaard, P.; Mathiesen, L. R.; Nielsen, J. O. Correlation between carbohydrate structures on the envelope glycoprotein gp120 of HIV-1 and HIV-2 and syncytium inhibition with lectins. *Aids* 1989, 3, 635-641.

29. Balzarini, J.; Schols, D.; Neyts, J.; Van Damme, E.; Peumans, W.; De Clercq, E. Alpha-(1-3)- and alpha-(1-6)-D-mannose-specific plant lectins are markedly inhibitory to human immunodeficiency virus and cytomegalovirus infections in vitro. *Antimicrob Agents Chemother* 1991, 35, 410-416.

30. Gattegno, L.; Ramdani, A.; Jouault, T.; Saffar, L.; Gluckman, J. C. Lectin-carbohydrate interactions and infectivity of human immunodeficiency virus type 1 (HIV-1) *AIDS Res Hum Retroviruses* 1992, 8, 27-37.

31. Hammar, L.; Hirsch, I.; Machado, A. A.; De Mareuil J.; Baillon, J. G.; Bolmont, C.; Chermann, J. C. Lectin-mediated effects on IIIV type 1 infection in vitro. *AIDS Res Hum Retroviruses* 1995, 11, 87-95.

32. Saifuddin, M.; Hart, M. L.; Gewurz, H.; Zhang, Y.; Spear, G. T. Interaction of mannose-binding lectin with primary isolates of human immunodeficiency virus type 1. *J Gen Virol* 2000, 81, 949-955.

33. Boyd, M. R.; Gustafson, K. R.; MeMahon, J. B.; Shoemaker, W H.; OKeefe, B. R.; Mori, T.; Gulakowski, R. J.; Wu, L.; Rivera, M. I.; Laurencot, C. M.; Currens, M. J.; Cardellina, J. H., 2nd; Buckheit, R. W., Jr.; Nara, P. L.; Pannell, L. K.; Sowder, R. C., 2nd; Henderson, L. E. Discovery of cyanovirin-N, a novel human immunodeficiency virus-inactivating protein that binds viral surface envelope glycoprotein gp120: potential applications to microbicide development. *Antimicrob Agents Chemother* 1997, 41, 1521-1530.

34. Dey, B.; Lemer, D. L.; Lusso, P.; Boyd, M. R.; Elder, J. H.; Berger, E. A. Multiple antiviral activities of cyanovirin-N: blocking of human immunodeficiency virus type 1 gp120 interaction with CD4 and coreceptor and inhibition of diverse enveloped viruses. *J Virol* 2000, 74, 4562-4569.

35. Bewley, C. A. Solution structure of a cyanovirin-N:Man alpha 1-2Man alpha complex: structural basis for high-affinity carbohydrate-mediated binding to gp120. *Structure (Camb)* 2001, 9, 931-940.

36. Bewley, C. A.; Otero-Quintero, S. The potent anti-HIV protein cyanovirin-N contains two novel carbohydrate binding sites that selectively bind to Man(8) D1D3 and Man(9) with nanomolar affinity implications for binding to the HIV envelope protein gp120. *J Am Chem Soc* 2001, 123, 3892-3902.

37. Bolmstedt, A. J.; O'Keefe, B. R.; Shenoy, S. R.; McMahon, J. B.; Boyd, M. R. Cyanovirin-N defines a new class of 38. Geijtenbeek, T. B.; Kwon, D. S.; Torensma, R.; van Vliet, S. J.; van Duijnhoven, G. C.; Middel, J.; Cornelissen, I. L.; Nottet, H. S.; KewalRamani, V. N., Littman, D. R.; Figdor, C. G.; van Kooyk, Y. DC-SIGN, a dendritic cell-specific HIV-1-binding protein that enhances trans-infection of T cells. *Cell* 2000, 100, 587-597.
39. Geijtenbeek, T. B.; Torensma, R.; van Vliet, S. J.; van Duijnhoven, G. C.; Adema, G. J.; van Kooyk:, Y.; Figdor, C. G. Identification of DC-SIGN, a novel dendritic cell-specific ICAM-3 receptor that supports primary immune responses. *Cell* 2000, 100, 575-585.
40. Pohlmann, S.; Soilleux, E. J.; Baribaud, F.; Leslie, G. J.; Morris, L. S.; Trowsdale, J.; Lee, B.; Coleman, N.; Doms, R. W. DC-SIGNR, a DC-SIGN homologue expressed in endothelial cells, binds to human and simian immunodeficiency viruses and activates infection in trans. *Proc Natl Acad Sci USA* 2001, 98, 2670-2675.
41. Mitchell, D. A.; Fadden, A. J.; Drickamer, K. A novel mechanism of carbohydrate recognition by the C-type lectins DC-SIGN and DC-SIGNR. Subunit organization and binding to multivalent ligands. *J Biol Chem* 2001, 276, 28939-28945.
42. Feinberg, H.; Mitchell, D. A.; Drickamer, K.; Weis, W. I. Structural basis for selective recognition of oligosaccharides by DC-SIGN and DC-SIGNR. *Science* 2001, 294, 2163-2166.
43. Wang, L. X.; Ni, J.; Singh, S. Carbohydrate-centered maleimide cluster as a new type of templates for multivalent peptide assembling: Synthesis of multivalent HIV-1 gp41 peptides. *Bioorg. Med. Chem.* 2002, in press.
44. Kudryashov, V., Kim, H. M.; Ragupathi, G.; Danishefsky, S. J.; Livingston, P. O.; Lloyd, K. O. Immunogenicity of synthetic conjugates of Lewis(y) oligosaccharide with proteins in mice: towards the design of anticancer vaccines. *Cancer Immunol Immunother* 1998, 45, 281-286.
45. Slovin, S. F.; Ragupathi, G.; Adluri, S.; Ungers, G.; Terry, K.; Kim, S.; Spassova, M.; Bornmann, W. G.; Fazzari, M.; Dantis, L.; Olkiewicz, K.; Lloyd, K. O.; Livingston, P. O.; Danishefsky, S. J.; Scher, H. I. Carbohydrate vaccines in cancer: immunogenicity of a fully synthetic globo H hexasaccharide conjugate in man. *Proc Natl Acad &Sci USA* 1999, 96, 5710-5715.
46. Wang, Z. O.; Williams, L. J.; Zhang, X. F.; Zatorski, A.; Kudryashov, V.; Ragupathi, G.; Spassova, M.; Borumarm, W.; Slovin, S. F.; Scher, H. I.; Livingston, P. O.; Lloyd, K. O.; Danishefsky, S. J. Polyclonal antibodies from patients immunized with a globo H-keyhole limpet hemocyanin vaccine: isolation, quantification, and characterization of immune responses by using totally synthetic immobilized tumor antigens. *Proc Natl Acad Sci USA* 2000, 97, 2719-2724.
47. Sabbatini, P. J.; Kudryashov, V.; Ragupathi, G.; Danishefsky, S. J.; Livingston, P. O.; Bornmann, W.; Spassova, M.; Zatorski, A.; Spriggs, D.; Aghajanian, C.; Soignet, S.; Peyton, M.; O'Flaherty, C.; Curtin, J.; Lloyd, K. O. Immunization of ovarian cancer patients with a synthetic Lewis (y)-protein conjugate vaccine: a phase 1 trial. *Int J Cancer* 2000, 87, 79-85.
48. Danishefsky, S. J.; Allen, J. W From the laboratory to the clinic: A retrospective on fully synthetic carbohydrate-based anticancer vaccines *Agnew. Chem. Int. Ed Engi.* 2000, 39, 836-863.
49. Kudryashov, V.; Glunz, P. W.; Williams, L. J.; Hintermanm, S.; Danishefsky, S. J.; Lloyd, K. O. Toward optimized carbohydrate-based anticancer vaccines: epitope clustering, carrier structure, and adjuvant all influence antibody responses Lewis (y) conjugates in mice. *Proc Natl Acad & Sci USA* 2001, 98, 3264-3269.
50. Gilewski, T.; Ragupathi, G.; Bhuta, S.; Williams, L. J.; Musselli, C.; Zhang, X. F.; Bencsath, K. P.; Panageas, K. S.; Chin, J.; Hudis, C. A.; Norton, L.; Houghton, A. N.; Livingston, P. O.; Danishefsky, S. J. Immunization of metastatic breast cancer patients with a fully synthetic globo H conjugate: a phase I trial. *Proc Natl Acad & Sci USA* 2001, 98, 3270-3275.
51. Allen, J. R.; Harris, C. R.; Danishefsky, S. J. Pursuit of optimal carbohydrate-based anticancer vaccines: preparation of a multiantigenic unimolecular glycopeptide containing the Tn, MBr1, and Lewis (y) antigens. *J Am Chem Soc.* 2001, 123, 1890-1897.
52. Ragupathi, G.; Cappello, S.; Yi, S. S.; Canter, D.; Spassova, M.; Bornmann, W. G.; Danishefsky, S. J.; Livingston, P. O. Comparison of antibody titers after immunization with monovalent or tetravalent KLH conjugate vaccines. *Vaccine* 2002, 20, 1030-1038.
53. Morley, S. L.; Pollard, A. J. Vaccine prevention of meningococcal disease, coining soon? *Vaccine* 2001, 20, 666-687.
54. Lis, H.; Sharon, N. Soybean agglutinin—a plant glycoprotein. Structure of the carbohydrate unit. *J Biol Chem* 1978, 253, 3468-3476.
55. Dorland, L.; van Halbeek, H.; Vleigenthart, J. F.; Lis, H.; Sharon, N. Primary structure of the carbohydrate chain of soybean agglutinin. A reinvestigation by high resolution $^1$H NMR spectroscopy. *J Biol Chem* 1981, 256, 7708-7711.
56. Wang, L. X.; Fang, J. Q.; Lee, Y. C. Chemoenzymatic synthesis of a high-mannose-type N-glycopeptide analog with C-glycosidic linkage. *Tetrahedron Lett.* 1996, 37, 1975-1978.
57. Wang, L. X.; Tang, M.; Suzuki, T.; Kitajima, K.; Inoue, Y; Inoue, S.; Fang, J. Q.; Lee, Y. C. Combined chemical and enzymatic synthesis of a C-glycopeptide and its inhibitory activity toward glycoamidases. *J Am. Chem. Soc.* 1997, 119, 11137-11146.
58. Ni, J.; Singh, S.; Wang, L. X. Improved preparation of perallylated cyclodextrins: facile synthesis of cyclodextrin-based polycationic and polyanionic compounds. *Carbohydr Res* 2002, 337, 217-220.
59. Sprengard, Ux.; Kretzschmar, G.; Bartnik, E.; Huls, C.; Kunz, H. Synthesis of an RGD-sialyl-Lewis glycoconjugates: A new highly active ligand for P-selectin. *Angew Chem. Intt. Ed Engl* 1995, 34, 990-993.
60. Cohen-Anisfeid, S. T.; Lansbury Jr., P. T. A practical, convergent method for glycopeptide synthesis. *J Am. Chem. Soc.* 1993, 115, 10531-10537.
61. Helling, F.; Shang, A.; Calves, M.; Zhang, S.; Ren, S.; Yu, R. K.; Oettgen, H. F.; Livingston, P. O. GD3 vaccines for melanoma: superior immunogenicity of keyhole limpet hemocyanin conjugate vaccines. *Cancer Res* 1994, 54, 197-203.
62. Helling, F.; Zhang, S.; Shang, A.; Adluri, S.; Calves, M.; Koganty, R.; Longenecker, B. M.; Yao, T. J.; Oettgen, H. F.; Livingston, P. O. GM2-KLH conjugate vaccine: increased immunogenicity in melanoma patients after administration with immunological adjuvant QS-21. *Cancer Res* 1995, 55, 2783-2788.
63. Kensil, C. R.; Patel, U.; Lennick, M.; Marciani, D. Separation and characterization of saponins with adjuvant activity from Quillaja saponaria Molina cortex. *J Immunol* 1991, 146, 431-437.

64. Pal, R.; DeVico, A.; Rittenhouse, S.; Sarngadharan, M. G. Conformational perturbation of the envelope glycoprotein gp120 of human immunodeficiency virus type 1 by soluble CD4 and the lectin succinyl Con A. *Virology* 1993, 194, 833-837.
65. DeVico, A. L.; Rahman, R.; Welch, J.; Crowley, R.; Lusso, P.; Sarngadharan, M. G.; Pal, R. Monoclonal antibodies raised against covalently crosslinked complexes of human immunodeficiency virus type 1 gp120 and CD4 receptor identify a novel complex-dependent epitope on gp 120. *Virology* 1995, 211, 583-588.
66. Fouts, T. R.; Tuskan, R. G.; Chada, S.; Hone, D. M.; Lewis, G. K. Construction and immunogenicity of *Salmonella typhiniurium* vaccine vectors that express HIV-1 gp120. *Vaccine* 1995, 13, 1697-1705.
67. Dear, E. S.; Li, X. L.; Moodily, T.; Ho, D. D. High concentrations of recombinant soluble CD4 are required to neutralize primary human immunodeficiency virus type 1 isolates. *Proc. Natl. Acad. Sci. USA.* 1990, 87, 6574-6578.
68. Connor, R. I.; Sheridan, K. B.; Ceradini, D.; Choe, S.; Landau, N. R. Change in coreceptor use coreceptor use correlates with disease progression in HIV-1 infected individuals. *J. Exp. Med* 1997, 185, 621-628.
69. Connor, R. I.; Mohri, H.; Cao, Y.; Ho, D. D. Increased viral burden and cytopathicity correlate temporally with CD4+ T-lymphocyte decline and clinical progression in human immunodeficiency virus type 1-infected individuals. *J Virol* 1993, 67, 1772-1777.
70. Vujcic, L. K.; Quinnan, G. V., Jr. Preparation and characterization of human HIV type 1 neutralizing reference sera. *AIDS Res. Hum. Retroviruses,* 1995, 11, 783-787.
71. a) Turnbull, W. B.; Stoddatt, J. F., *J. Biotechnol.* 2002, 90, 231-255. b) Lindhorst, T. K., *Topics in Curr. Chem.* 2002, 218, 200-235. (c) Roy, R., *Curr. Opin. Struct Biol* 1996, 6, 692-702.
72. Kitov, P. I.; Sadowska, J. M.; Mulvey, G.; Armstrong, G. D.; Ling, H.; Pannu, N. S.; Read, R. J.; Bundle, D. R., *Nature* 2000, 403, 669-672.
73. Wang, L. x.; Ni, J.; Singh, S., *Bioorg. Med Chem.* 2002, in press.
74. Lis, H.; Sharon, N., *J Biol. Chem.* 1978, 253, 3468-3476.
75 Duncan, R. J.; Weston, P. D.; Wrigglesworth, R., *Anal. Biochem.* 1983, 132, 68-73.
76. Mizuochi, T., Matthews, T. J., Kato, M., Hamako, J., Titani, K., Solomon, J., and Feizi, T. (1990) *J Biol Chem* 265, 8519-8524.
77. Geyer, H., Holschbach, C., Hunsmann, G., and Schneider, J. (1988) *J Biol Chem* 263, 11760-11767.
78. Zhu, X., Borchers, C., Bienstock, R. J., and Tomer, K. B. (2000) *Biochemistry* 39, 11194-11204.
79. Fujita, K., Tanaka, N., Sano, M., Kato, I., Asada, Y., and Takegawa, K. (2000) *Biochem. Biophys. Res. Commun.* 267, 134-138.
80. Huang, C. C., Mayer, H. E., and Montgomery, R. (1970) *Carbohydr. Res.* 13, 127-137.
81. Sanders, R. W., Venturi, M., Schiffner, L., Kalyanaraman, R., Katinger, H., Lloyd, K. O., Kwong, P. D., and Moore, J. P. (2002) *J Virol* 76, 7293-7305.
82. Scanlan, C. N., Pantophlet, R., Wormald, M. R., Ollmann Saphire, E., Stanfield, R, Wilson, I. A., Katinger, H., Dwek, R. A., Rudd, P. M., and Burton, D. R. (2002) *J Virol* 76, 7306-7321.
83. Wang, L. X., Ni, J., and Singh, S. (2003) *Bioorg. Med. Chem.* 11, 129-136.
84. Ni, J., Singh, S., and Wang, L. X. (2003) *Bioconjug Chem* 14, 232-238.
85. Duncan, R. J., Weston, P. D., and Wrigglesworth, R. (1983) *Anal Biochem* 132, 68-73.

That which is claimed is:

1. A high-mannose oligosacoharide cluster that mimics a carbohydrate epitope on gp120 comprising four high-mannose oligosaccharides positioned on a cyclic core scaffolding framework, wherein the cyclic core scaffolding framework comprises monosaccharides, or cyclic organic compounds, wherein the four high-mannose oligosaccharides are $Man_9$, and wherein the positioning of high-mannose oligosaccharides on the cyclic core scaffolding framework mimics the carbohydrate epitope on gp120 having affinity for 2G12 antibodies.

2. The high-mannose oligosaccharide cluster according to claim 1, further comprising an immunogenic protein conjugated to the high-mannose oligosaccharide cluster thereby producing a high-mannose oligosaccharide/protein cluster.

3. The high-mannose oligosacoharide cluster of claim 2, wherein the immunogenic protein is selected from the group consisting of keyhole limpet hemocyanin, tetanus toxoid, diphtheria toxoid, bovine serum albumin, ovalbumin, thyroglobulin, myoglobin, cholera toxin β-subunit, immunoglobulin and/or tuberculosis purified protein derivative.

4. The high-mannose oligosaccharide cluster of claim 2 comprising four $Man_9$ covalently attached to a galactose scaffolding framework, wherein the immunogenic protein comprises keyhole limpet hemocyanin.

5. A pharmaceutical composition comprising the high-mannose oligosaccharide cluster of claim 1.

6. A method for generating a high-mannose oligosaccharide cluster, the method comprising:
covalently attaching four high-mannose oligosaccharide chain to a cyclic core scaffolding framework, wherein the cyclic core scaffolding framework comprises monosaccharides, or cyclic organic compounds, wherein the four high-mannose oligosaccharides are $Man_9$, and wherein the positioning of high-mannose oligosaccharides on the cyclic core scaffolding framework mimics a carbohydrate epitope on gp120 having affinity for 2G12 antibodies.

7. The method according to claim 6, wherein the high-mannose oligosaccharide chain is extracted from the digestion of soybean agglutinin or produced by chemical synthesis.

8. The method of claim 6, further comprising conjugating an immunogenic protein to the high-mannose oligosaccharide cluster.

9. A method of inducing production of HIV antibodies that exhibit affinity for a conserved cluster of oligomannose sugars on gp120, the method comprising:
administering to an animal the high-mannose oligosaccharide according to claim 2 in an amount sufficient to induce production of antisera specific for the high-mannose oligosaccharide; and collecting the antisera.

10. A method for detecting candidate compounds that potentially interact with a conserved cluster of oligomannose sugars on gp120, the process comprising:
contacting the candidate compound with the high-mannose oligosaccharide cluster according to claim 1; and determining the binding affinity of the candidate compound for high-mannose oligosaccharide cluster.

* * * * *